United States Patent
Felder et al.

(10) Patent No.: US 9,074,016 B2
(45) Date of Patent: Jul. 7, 2015

(54) G PROTEIN-RELATED KINASE MUTANTS IN ESSENTIAL HYPERTENSION

(75) Inventors: Robin A. Felder, Charlottesville, VA (US); Pedro Jose, Mason Neck, VA (US)

(73) Assignees: Robin A. Felde, Charlottesville, VA (US); Pedro Jose, Mason Neck, VA (US)

( * ) Notice: Subject to any disclaimer, the term of this patent is extended or adjusted under 35 U.S.C. 154(b) by 661 days.

(21) Appl. No.: 12/315,338

(22) Filed: Dec. 1, 2008

(65) Prior Publication Data

US 2010/0313286 A1 Dec. 9, 2010

Related U.S. Application Data

(60) Continuation of application No. 10/677,983, filed on Oct. 2, 2003, now abandoned, which is a division of application No. 09/614,748, filed on Jul. 12, 2000, now Pat. No. 6,660,474, which is a continuation of application No. PCT/US99/00663, filed on Jan. 12, 1999.

(60) Provisional application No. 60/071,199, filed on Jan. 12, 1998, provisional application No. 60/098,279, filed on Aug. 28, 1998.

(51) Int. Cl.
*C07K 14/72* (2006.01)

(52) U.S. Cl.
CPC .......... *C07K 14/723* (2013.01); *A01K 2217/056* (2013.01); *A01K 2217/05* (2013.01)

(58) Field of Classification Search
CPC .............................................. A01K 2217/056
See application file for complete search history.

(56) References Cited

PUBLICATIONS

Sigmund, C. (2000) Viewpoint: Are studies in genetically altered mice out of control? Arterioscler. Thromb. Vasc. Biology 20: 1425-1429.*
Wall, RJ (1996) Transgenic livestock: Progress and prospects for the future. Theriogenology 45: 57-68.*
Elseth et al. Principles of Modern Genetics pp. 542-545 1994.
Casari et al. Hypertension 25(3):320-326 (1995).
Virlon et al. Endocrinilogy 139(5):2784-2795 (1998).
Courjault-Gautier et al., J. Am. Soc. Nephrol. 5:1949-1963 (1994).
Detrisac, et al., Kidney Int. 25:383-390 (1984).
Jose et al., Pharmacol Ther 80:149-182 (1998).
Ng et al., Eur. J. Pharmacol. 267:7-19 (1994).
Premont, et al., FASEB J. 9:175-182 (1995).
Palczewski, Protein Sci. 3:1355-1361 (1994).
Inglese, et al., J. Biol. Chem. 268:23735-23738 (1993).
Gros, J. Clin. Invest. 99(9):2087-2093 (1997).
Ambrose, et al., Hum. Mol. Genet. 1:697-703 (1993).
Sallese et al., Biochem. Biophys. Res. Commun. 199:848-854 (1994).
Menard, et al., Biochemistry 35(13):4155-4160 (1996).
Loudon, et al., J. Biol. Chem. 272(43);27422-27427 (1997).
Premont, et al., J. Biol. Chem. 271(11):6403-6410 (1996).
Albrecht, et al., J. Clin. Invest. 97(10):2283-2288 (1996).
Ohbu, et al., American J. of Physiology 268:R231-R235 (1995).
Eisner, et al., Am. J. Physiol. 273:R317-R323 (1997).
Jin, et al., Am. J. Physiol. 273:C1623-C1631 (1997).
Woost, et al., Kidney International 50:125-134 (1996).
Chen, et al., Kidney International 49:153-157 (1996).
Racusen, et al., Kidney International 48:536-543 (1995).
Ryan, et al., Kidney International 45:48-57 (1994).
Felder et al. (2002) G protein-coupled receptor kinase gene variants in human essential hypertension. PNAS 99(6): 3872-3877.
Ju et al. (1991) Conversion of the interleukin 1 receptor antagonist into an agonist by site-specific mutagenesis. Proc. Natl. Acad. Sci. USA 88: 2658-2662.
Pakula et al. (1989) Genetic analysis of protein stability and function. Annu. Rev. Genet. 23: 289-310.
Sallese et al. (1997) G protein-coupled receptor kinase GRK4: Molecular analysis of the four isoforms and ultrastructural localization in spermatozoa and germinal cells. J. Biol. Chem. 272(15): 10188-10195 (Apr. 11, 1997).
Skolnick et al. (2000) From genes to protein structure and function: novel applications of computational approaches in the genomic era. TIBTECH 18: 34-39.
Witkowski et al. (1999) Conversion of a beta-ketoacyl synthase to a malonyl decarboxylase by replacement of the active-site cystein with glutamine. Biochemistry 38: 11643-11650.
Yamaguchi et al. (1993) Expression of dopamine D1A receptor gene in proximal tubule of rat kidneys. Am. J. Physiol. Renal Physiol. 264: 280-285 (abstract only).
Racusen Lorraine C et al: "Cell lines with extended in vitro growth potential from human renal proximal tubule: Characterization, response to inducers, and comparison with established cell lines" Journal of Laboratory and Clinical Medicine, vol. 129, No. 3, 1997, pp. 318-329, XP002502836 ISSN: 0022-2143.
European Search Report, EP 08162553.

* cited by examiner

*Primary Examiner* — Anoop Singh
*Assistant Examiner* — David A Montanari
(74) *Attorney, Agent, or Firm* — Lerner, David, Littenberg, Krumholz & Mentlik, LLP

(57) ABSTRACT

Disclosed are methods for identifying individuals predisposed to essential hypertension and related conditions such as salt sensitivity by detecting the presence of polymorphic or mutant forms of the GRK4 gene, or its expression product. Also disclosed are methods for identifying polymorphic or mutant GRK4s in individuals known to be suffering from such conditions, as well as methods and compositions for conducting drug discovery and therapeutic intervention.

5 Claims, 5 Drawing Sheets

SEQUENCE LISTING

```
<160> NUMBER OF SEQ ID NOS: 34

<210> SEQ ID NO 1
<211> LENGTH: 578
<212> TYPE: PRT
<213> ORGANISM: Homo sapiens

<400> SEQUENCE: 1

Met Glu Leu Glu Asn Ile Val Ala Asn Ser Leu Leu Lys Ala Arg
  1               5                  10                  15

Gln Gly Gly Tyr Gly Lys Lys Ser Gly Arg Ser Lys Lys Trp Lys Glu
                 20                  25                  30

Ile Leu Thr Leu Pro Pro Val Ser Gln Cys Ser Glu Leu Arg His Ser
                 35                  40                  45

Ile Glu Lys Asp Tyr Ser Ser Leu Cys Asp Lys Gln Pro Ile Gly Arg
         50                  55                  60

Arg Leu Phe Arg Gln Phe Cys Asp Thr Lys Pro Thr Leu Lys Arg His
 65                  70                  75                  80

Ile Glu Phe Leu Asp Ala Val Ala Glu Tyr Glu Val Ala Asp Asp Glu
                 85                  90                  95

Asp Arg Ser Asp Cys Gly Leu Ser Ile Leu Asp Arg Phe Phe Asn Asp
                100                 105                 110

Lys Leu Ala Ala Pro Leu Pro Glu Ile Pro Pro Asp Val Val Thr Glu
            115                 120                 125

Cys Arg Leu Gly Leu Lys Glu Glu Asn Pro Ser Lys Lys Ala Phe Glu
    130                 135                 140

Glu Cys Thr Arg Val Ala His Asn Tyr Leu Arg Gly Glu Pro Phe Glu
145                 150                 155                 160

Glu Tyr Gln Glu Ser Ser Tyr Phe Ser Gln Phe Leu Gln Trp Lys Trp
                165                 170                 175

Leu Glu Arg Gln Pro Val Thr Lys Asn Thr Phe Arg His Tyr Arg Val
            180                 185                 190

Leu Gly Lys Gly Gly Phe Gly Glu Val Cys Ala Cys Gln Val Arg Ala
        195                 200                 205

Thr Gly Lys Met Tyr Ala Cys Lys Lys Leu Gln Lys Lys Arg Ile Lys
    210                 215                 220

Lys Arg Lys Gly Glu Ala Met Ala Leu Asn Glu Lys Arg Ile Leu Glu
225                 230                 235                 240

Lys Val Gln Ser Arg Phe Val Val Ser Leu Ala Tyr Ala Tyr Glu Thr
                245                 250                 255
```

```
Lys Asp Ala Leu Cys Leu Val Leu Thr Ile Met Asn Gly Gly Asp Leu
                260                 265                 270

Lys Phe His Ile Tyr Asn Leu Gly Asn Pro Gly Phe Asp Glu Gln Arg
            275                 280                 285

Ala Val Phe Tyr Ala Ala Glu Leu Cys Cys Gly Leu Glu Asp Leu Gln
        290                 295                 300

Arg Glu Arg Ile Val Tyr Arg Asp Leu Lys Pro Glu Asn Ile Leu Leu
305                 310                 315                 320

Asp Asp Arg Gly His Ile Arg Ile Ser Asp Leu Gly Leu Ala Thr Glu
                325                 330                 335

Ile Pro Glu Gly Gln Arg Val Arg Gly Arg Val Gly Thr Val Gly Tyr
            340                 345                 350

Met Ala Pro Glu Val Val Asn Asn Glu Lys Tyr Thr Phe Ser Pro Asp
        355                 360                 365

Trp Trp Gly Leu Gly Cys Leu Ile Tyr Glu Met Ile Gln Gly His Ser
370                 375                 380

Pro Phe Lys Lys Tyr Lys Glu Lys Val Lys Trp Glu Glu Val Asp Gln
385                 390                 395                 400

Arg Ile Lys Asn Asp Thr Glu Glu Tyr Ser Glu Lys Phe Ser Glu Asp
                405                 410                 415

Ala Lys Ser Ile Cys Arg Met Leu Leu Thr Lys Asn Pro Ser Lys Arg
            420                 425                 430

Leu Gly Cys Arg Gly Glu Gly Ala Gly Val Lys Gln His Pro Val
        435                 440                 445

Phe Lys Asp Ile Asn Phe Arg Arg Leu Glu Ala Asn Met Leu Glu Pro
450                 455                 460

Pro Phe Cys Pro Asp Pro His Ala Val Tyr Cys Lys Asp Val Leu Asp
465                 470                 475                 480

Ile Glu Gln Phe Ser Ala Val Lys Gly Ile Tyr Leu Asp Thr Ala Asp
                485                 490                 495

Glu Asp Phe Tyr Ala Arg Phe Ala Thr Gly Cys Val Ser Ile Pro Trp
            500                 505                 510

Gln Asn Glu Met Ile Glu Ser Gly Cys Phe Lys Asp Ile Asn Lys Ser
        515                 520                 525

Glu Ser Glu Glu Ala Leu Pro Leu Asp Leu Asp Lys Asn Ile His Thr
530                 535                 540

Pro Val Ser Arg Pro Asn Arg Gly Phe Phe Tyr Arg Leu Phe Arg Arg
545                 550                 555                 560

Gly Gly Cys Leu Thr Met Val Pro Ser Glu Lys Glu Val Glu Pro Lys
                565                 570                 575

Gln Cys

<210> SEQ ID NO 2
<211> LENGTH: 546
<212> TYPE: PRT
<213> ORGANISM: Homo sapiens

<400> SEQUENCE: 2

Met Glu Leu Glu Asn Ile Val Ala Asn Ser Leu Leu Leu Lys Ala Arg
1               5                   10                  15

Gln Glu Lys Asp Tyr Ser Ser Leu Cys Asp Lys Gln Pro Ile Gly Arg
            20                  25                  30

Arg Leu Phe Arg Gln Phe Cys Asp Thr Lys Pro Ile Leu Lys Arg His
        35                  40                  45
```

-continued

```
Ile Glu Phe Leu Asp Ala Val Ala Glu Tyr Glu Val Ala Asp Asp Glu
    50                  55                  60
Asp Arg Ser Asp Cys Gly Leu Ser Ile Leu Asp Arg Phe Phe Asn Asp
65                  70                  75                  80
Lys Leu Ala Ala Pro Leu Pro Glu Ile Pro Pro Asp Val Val Thr Glu
                85                  90                  95
Cys Arg Leu Gly Leu Lys Glu Glu Asn Pro Ser Lys Lys Ala Phe Glu
            100                 105                 110
Glu Cys Thr Arg Val Ala His Asn Tyr Leu Arg Gly Glu Pro Phe Glu
            115                 120                 125
Glu Tyr Gln Glu Ser Ser Tyr Phe Ser Gln Phe Leu Gln Trp Lys Trp
    130                 135                 140
Leu Glu Arg Gln Pro Val Thr Lys Asn Thr Phe Arg His Tyr Arg Val
145                 150                 155                 160
Leu Gly Lys Gly Gly Phe Gly Glu Val Cys Ala Cys Gln Val Arg Ala
                165                 170                 175
Thr Gly Lys Met Tyr Ala Cys Lys Lys Leu Gln Lys Lys Arg Ile Lys
            180                 185                 190
Lys Arg Lys Gly Glu Ala Met Ala Leu Asn Glu Lys Arg Ile Leu Glu
            195                 200                 205
Lys Val Gln Ser Arg Phe Val Val Ser Leu Ala Tyr Ala Tyr Glu Thr
    210                 215                 220
Lys Asp Ala Leu Cys Leu Val Leu Thr Ile Met Asn Gly Gly Asp Leu
225                 230                 235                 240
Lys Phe His Ile Tyr Asn Leu Gly Asn Pro Gly Phe Asp Glu Gln Arg
                245                 250                 255
Ala Val Phe Tyr Ala Ala Glu Leu Cys Cys Gly Leu Glu Asp Leu Gln
            260                 265                 270
Arg Glu Arg Ile Val Tyr Arg Asp Leu Lys Pro Glu Asn Ile Leu Leu
            275                 280                 285
Asp Asp Arg Gly His Ile Arg Ile Ser Asp Leu Gly Leu Ala Thr Glu
    290                 295                 300
Ile Pro Glu Gly Gln Arg Val Arg Gly Arg Val Gly Thr Val Gly Tyr
305                 310                 315                 320
Met Ala Pro Glu Val Val Asn Asn Glu Lys Tyr Thr Phe Ser Pro Asp
                325                 330                 335
Trp Trp Gly Leu Gly Cys Leu Ile Tyr Glu Met Ile Gln Gly His Ser
            340                 345                 350
Pro Phe Lys Lys Tyr Lys Glu Lys Val Lys Trp Glu Glu Val Asp Gln
            355                 360                 365
Arg Ile Lys Asn Asp Thr Glu Glu Tyr Ser Glu Lys Phe Ser Glu Asp
    370                 375                 380
Ala Lys Ser Ile Cys Arg Met Leu Leu Thr Lys Asn Pro Ser Lys Arg
385                 390                 395                 400
Leu Gly Cys Arg Gly Glu Gly Ala Ala Gly Val Lys Gln His Pro Val
                405                 410                 415
Phe Lys Asp Ile Asn Phe Arg Arg Leu Glu Ala Asn Met Leu Glu Pro
            420                 425                 430
Pro Phe Cys Pro Asp Pro His Ala Val Tyr Cys Lys Asp Val Leu Asp
            435                 440                 445
Ile Glu Gln Phe Ser Ala Val Lys Gly Ile Tyr Leu Asp Thr Ala Asp
    450                 455                 460
Glu Asp Phe Tyr Ala Arg Phe Ala Thr Gly Cys Val Ser Ile Pro Trp
```

```
                    465                 470                 475                 480
              Gln Asn Glu Met Ile Glu Ser Gly Cys Phe Lys Asp Ile Asn Lys Ser
                              485                 490                 495

Glu Ser Glu Glu Ala Leu Pro Leu Asp Leu Asp Lys Asn Ile His Thr
                          500                 505                 510

Pro Val Ser Arg Pro Asn Arg Gly Phe Phe Tyr Arg Leu Phe Arg Arg
                          515                 520                 525

Gly Gly Cys Leu Thr Met Val Pro Ser Glu Lys Glu Val Glu Pro Lys
                      530                 535                 540

Gln Cys
              545

<210> SEQ ID NO 3
<211> LENGTH: 532
<212> TYPE: PRT
<213> ORGANISM: Homo sapiens

<400> SEQUENCE: 3

Met Glu Leu Glu Asn Ile Val Ala Asn Ser Leu Leu Leu Lys Ala Arg
 1               5                  10                  15

Gln Gly Gly Tyr Gly Lys Lys Ser Gly Arg Ser Lys Lys Trp Lys Glu
             20                  25                  30

Ile Leu Thr Leu Pro Pro Val Ser Gln Cys Ser Glu Leu Arg His Ser
         35                  40                  45

Ile Glu Lys Asp Tyr Ser Ser Leu Cys Asp Lys Gln Pro Ile Gly Arg
     50                  55                  60

Arg Leu Phe Arg Gln Phe Cys Asp Thr Lys Pro Ile Leu Lys Arg His
 65                  70                  75                  80

Ile Glu Phe Leu Asp Ala Val Ala Glu Tyr Glu Val Ala Asp Asp Glu
                 85                  90                  95

Asp Arg Ser Asp Cys Gly Leu Ser Ile Leu Asp Arg Phe Phe Asn Asp
             100                 105                 110

Lys Leu Ala Ala Pro Leu Pro Glu Ile Pro Pro Asp Val Val Thr Glu
         115                 120                 125

Cys Arg Leu Gly Leu Lys Glu Glu Asn Pro Ser Lys Lys Ala Phe Glu
     130                 135                 140

Glu Cys Thr Arg Val Ala His Asn Tyr Leu Arg Gly Glu Pro Phe Glu
145                 150                 155                 160

Glu Tyr Gln Glu Ser Ser Tyr Phe Ser Gln Phe Leu Gln Trp Lys Trp
                165                 170                 175

Leu Glu Arg Gln Pro Val Ile Lys Asn Thr Phe Arg His Tyr Arg Val
            180                 185                 190

Leu Gly Lys Gly Gly Phe Gly Glu Val Cys Ala Cys Gln Val Arg Ala
        195                 200                 205

Thr Gly Lys Met Tyr Ala Cys Lys Lys Leu Gln Lys Lys Arg Ile Lys
    210                 215                 220

Lys Arg Lys Gly Glu Ala Met Ala Leu Asn Glu Lys Arg Ile Leu Glu
225                 230                 235                 240

Lys Val Gln Ser Arg Phe Val Val Ser Leu Ala Tyr Ala Tyr Glu Thr
                245                 250                 255

Lys Asp Ala Leu Cys Leu Val Leu Thr Ile Met Asn Gly Gly Asp Leu
            260                 265                 270

Lys Phe His Ile Tyr Asn Leu Gly Asn Pro Gly Phe Asp Glu Gln Arg
        275                 280                 285
```

```
Ala Val Phe Tyr Ala Ala Glu Leu Cys Cys Gly Leu Glu Asp Leu Gln
            290                 295                 300

Arg Glu Arg Ile Val Tyr Arg Asp Leu Lys Pro Glu Asn Ile Leu Leu
305                 310                 315                 320

Asp Asp Arg Gly His Ile Arg Ile Ser Asp Leu Gly Leu Ala Thr Glu
                325                 330                 335

Ile Pro Glu Gly Gln Arg Val Arg Gly Arg Val Gly Thr Val Gly Tyr
            340                 345                 350

Met Ala Pro Glu Val Val Asn Asn Glu Lys Tyr Thr Phe Ser Pro Asp
        355                 360                 365

Trp Trp Gly Leu Gly Cys Leu Ile Tyr Glu Met Ile Gln Gly His Ser
370                 375                 380

Pro Phe Lys Lys Tyr Lys Glu Lys Val Lys Trp Glu Glu Val Asp Gln
385                 390                 395                 400

Arg Ile Lys Asn Asp Thr Glu Glu Tyr Ser Glu Lys Phe Ser Glu Asp
                405                 410                 415

Ala Lys Ser Ile Cys Arg Met Leu Leu Thr Lys Asn Pro Ser Lys Arg
            420                 425                 430

Leu Gly Cys Arg Gly Glu Gly Ala Ala Gly Val Lys Gln His Pro Val
        435                 440                 445

Phe Lys Asp Ile Asn Phe Arg Arg Leu Glu Ala Asn Met Leu Glu Pro
    450                 455                 460

Pro Phe Cys Pro Asp Pro His Ala Val Tyr Cys Lys Asp Val Leu Asp
465                 470                 475                 480

Ile Glu Gln Phe Ser Ala Val Lys Gly Ile Tyr Leu Asp Thr Ala Asp
                485                 490                 495

Glu Asp Phe Tyr Ala Arg Phe Ala Thr Gly Cys Val Ser Ile Pro Trp
            500                 505                 510

Gln Asn Glu Gly Cys Leu Thr Met Val Pro Ser Glu Lys Glu Val Glu
        515                 520                 525

Pro Lys Gln Cys
        530

<210> SEQ ID NO 4
<211> LENGTH: 500
<212> TYPE: PRT
<213> ORGANISM: Homo sapiens

<400> SEQUENCE: 4

Met Glu Leu Glu Asn Ile Val Ala Asn Ser Leu Leu Leu Lys Ala Arg
1               5                   10                  15

Gln Glu Lys Asp Tyr Ser Ser Leu Cys Asp Lys Gln Pro Ile Gly Arg
            20                  25                  30

Arg Leu Phe Arg Gln Phe Cys Asp Thr Lys Pro Thr Leu Lys Arg His
        35                  40                  45

Ile Glu Phe Leu Asp Ala Val Ala Glu Tyr Glu Val Ala Asp Asp Glu
    50                  55                  60

Asp Arg Ser Asp Cys Gly Leu Ser Ile Leu Asp Arg Phe Phe Asn Asp
65                  70                  75                  80

Lys Leu Ala Ala Pro Leu Pro Glu Ile Pro Pro Asp Val Thr Glu
                85                  90                  95

Cys Arg Leu Gly Leu Lys Glu Glu Asn Pro Ser Lys Lys Ala Phe Glu
            100                 105                 110

Glu Cys Thr Arg Val Ala His Asn Tyr Leu Arg Gly Glu Pro Phe Glu
        115                 120                 125
```

Glu Tyr Gln Glu Ser Ser Tyr Phe Ser Gln Phe Leu Gln Trp Lys Trp
            130                 135                 140

Leu Glu Arg Gln Pro Val Thr Lys Asn Thr Phe Arg His Tyr Arg Val
145                 150                 155                 160

Leu Gly Lys Gly Phe Gly Glu Val Cys Ala Cys Gln Val Arg Ala
                165                 170                 175

Thr Gly Lys Met Tyr Ala Cys Lys Lys Leu Gln Lys Lys Arg Ile Lys
                180                 185                 190

Lys Arg Lys Gly Glu Ala Met Ala Leu Asn Glu Lys Arg Ile Leu Glu
            195                 200                 205

Lys Val Gln Ser Arg Phe Val Val Ser Leu Ala Tyr Ala Tyr Glu Thr
            210                 215                 220

Lys Asp Ala Leu Cys Leu Val Leu Thr Ile Met Asn Gly Gly Asp Leu
225                 230                 235                 240

Lys Phe His Ile Tyr Asn Leu Gly Asn Pro Gly Phe Asp Glu Gln Arg
                245                 250                 255

Ala Val Phe Tyr Ala Ala Glu Leu Cys Cys Gly Leu Glu Asp Leu Gln
                260                 265                 270

Arg Glu Arg Ile Val Tyr Arg Asp Leu Lys Pro Glu Asn Ile Leu Leu
            275                 280                 285

Asp Asp Arg Gly His Ile Arg Ile Ser Asp Leu Gly Leu Ala Thr Glu
290                 295                 300

Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
                325                 330                 335

Trp Trp Gly Leu Gly Cys Leu Ile Tyr Glu Met Ile Gln Gly His Ser
                340                 345                 350

Pro Phe Lys Lys Tyr Lys Glu Lys Val Lys Trp Glu Glu Val Asp Gln
            355                 360                 365

Arg Ile Lys Asn Asp Thr Glu Glu Tyr Ser Glu Lys Phe Ser Glu Asp
            370                 375                 380

Ala Lys Ser Ile Cys Arg Met Leu Leu Thr Lys Asn Pro Ser Lys Arg
385                 390                 395                 400

Leu Gly Cys Arg Gly Glu Gly Ala Ala Gly Val Lys Gln His Pro Val
                405                 410                 415

Phe Lys Asp Ile Asn Phe Arg Arg Leu Glu Ala Asn Met Leu Glu Pro
                420                 425                 430

Pro Phe Cys Pro Asp Pro His Ala Val Tyr Cys Lys Asp Val Leu Asp
                435                 440                 445

Ile Glu Gln Phe Ser Ala Val Lys Gly Ile Tyr Leu Asp Thr Ala Asp
            450                 455                 460

Glu Asp Phe Tyr Ala Arg Phe Ala Thr Gly Cys Val Ser Ile Pro Trp
465                 470                 475                 480

Gln Asn Glu Gly Cys Leu Thr Met Val Pro Ser Glu Lys Glu Val Glu
                485                 490                 495

Pro Lys Gln Cys
            500

<210> SEQ ID NO 5
<211> LENGTH: 486
<212> TYPE: PRT
<213> ORGANISM: Homo sapiens

```
<400> SEQUENCE: 5

Met Glu Leu Glu Asn Ile Val Ala Asn Ser Leu Leu Lys Ala Arg
  1               5                  10                  15

Gln Gly Gly Tyr Gly Lys Lys Ser Gly Arg Ser Lys Lys Trp Lys Glu
             20                  25                  30

Ile Leu Thr Leu Pro Pro Val Ser Gln Cys Ser Glu Leu Arg His Ser
             35                  40                  45

Ile Glu Lys Asp Tyr Ser Ser Leu Cys Asp Lys Gln Pro Ile Gly Arg
         50                  55                  60

Arg Leu Phe Arg Gln Phe Cys Asp Thr Lys Pro Thr Leu Lys Arg His
 65              70                  75                  80

Ile Glu Phe Leu Asp Ala Val Ala Glu Tyr Glu Val Ala Asp Asp Glu
                 85                  90                  95

Asp Arg Ser Asp Cys Gly Leu Ser Ile Leu Asp Arg Phe Phe Asn Asp
            100                 105                 110

Lys Leu Ala Ala Pro Leu Pro Glu Ile Pro Pro Asp Val Val Thr Glu
            115                 120                 125

Cys Arg Leu Gly Leu Lys Glu Glu Asn Pro Ser Lys Lys Ala Phe Glu
130                 135                 140

Glu Cys Thr Arg Val Ala His Asn Tyr Leu Arg Gly Glu Pro Phe Glu
145                 150                 155                 160

Glu Tyr Gln Glu Ser Ser Tyr Phe Ser Gln Phe Leu Gln Trp Lys Trp
                165                 170                 175

Leu Glu Arg Gln Pro Val Thr Lys Asn Thr Phe Arg His Tyr Arg Val
            180                 185                 190

Leu Gly Lys Gly Gly Phe Gly Glu Val Cys Ala Cys Gln Val Arg Ala
        195                 200                 205

Thr Gly Lys Met Tyr Ala Cys Lys Lys Leu Gln Lys Lys Arg Ile Lys
        210                 215                 220

Lys Arg Lys Gly Glu Ala Met Ala Leu Asn Glu Lys Arg Ile Leu Glu
225                 230                 235                 240

Lys Val Gln Ser Arg Phe Val Val Ser Leu Ala Tyr Ala Tyr Glu Thr
                245                 250                 255

Lys Asp Ala Leu Cys Leu Val Leu Thr Ile Met Asn Gly Gly Asp Leu
            260                 265                 270

Lys Phe His Ile Tyr Asn Leu Gly Asn Pro Gly Phe Asp Glu Gln Arg
        275                 280                 285

Ala Val Phe Tyr Ala Ala Glu Leu Cys Cys Gly Leu Glu Asp Leu Gln
        290                 295                 300

Arg Glu Arg Ile Val Tyr Arg Asp Leu Lys Pro Glu Asn Ile Leu Leu
305                 310                 315                 320

Asp Asp Arg Gly His Ile Arg Ile Ser Asp Leu Gly Leu Ala Thr Glu
                325                 330                 335

Ile Pro Glu Gly Gln Arg Val Arg Gly Arg Val Gly Thr Val Gly Tyr
            340                 345                 350

Met Ala Pro Glu Val Val Asn Asn Glu Lys Tyr Thr Phe Ser Pro Asp
            355                 360                 365

Trp Trp Gly Leu Gly Cys Leu Ile Tyr Glu Met Ile Gln Gly His Ser
        370                 375                 380

Pro Phe Lys Lys Tyr Lys Glu Lys Val Lys Trp Glu Glu Val Asp Gln
385                 390                 395                 400

Arg Ile Lys Asn Asp Thr Glu Glu Tyr Ser Glu Lys Phe Ser Glu Asp
                405                 410                 415
```

```
Ala Lys Ser Ile Cys Arg Met Pro His Ala Val Tyr Cys Lys Asp Val
            420                 425                 430

Leu Asp Ile Glu Gln Phe Ser Ala Val Lys Gly Ile Tyr Leu Asp Thr
        435                 440                 445

Ala Asp Glu Asp Phe Tyr Ala Arg Phe Ala Thr Gly Cys Val Ser Ile
450                 455                 460

Pro Trp Gln Asn Glu Gly Cys Leu Thr Met Val Pro Ser Lys Glu
465                 470                 475                 480

Val Glu Pro Lys Gln Cys
                485

<210> SEQ ID NO 6
<211> LENGTH: 454
<212> TYPE: PRT
<213> ORGANISM: Homo sapiens

<400> SEQUENCE: 6

Met Glu Leu Glu Asn Ile Val Ala Asn Ser Leu Leu Leu Lys Ala Arg
  1               5                  10                  15

Gln Glu Lys Asp Tyr Ser Ser Leu Cys Asp Lys Gln Pro Ile Gly Arg
             20                  25                  30

Arg Leu Phe Arg Gln Phe Cys Asp Thr Lys Pro Thr Leu Lys Arg His
         35                  40                  45

Ile Glu Phe Leu Asp Ala Val Ala Glu Tyr Glu Val Ala Asp Asp Glu
     50                  55                  60

Asp Arg Ser Asp Cys Gly Leu Ser Ile Leu Asp Arg Phe Phe Asn Asp
 65                  70                  75                  80

Lys Leu Ala Ala Pro Leu Pro Glu Ile Pro Pro Asp Val Val Thr Glu
                 85                  90                  95

Cys Arg Leu Gly Leu Lys Glu Glu Asn Pro Ser Lys Lys Ala Phe Glu
            100                 105                 110

Glu Cys Thr Arg Val Ala His Asn Tyr Leu Arg Gly Glu Pro Phe Glu
        115                 120                 125

Glu Tyr Gln Glu Ser Ser Tyr Phe Ser Gln Phe Leu Gln Trp Lys Trp
    130                 135                 140

Leu Glu Arg Gln Pro Val Thr Lys Asn Thr Phe Arg His Tyr Arg Val
145                 150                 155                 160

Leu Gly Lys Gly Gly Phe Gly Glu Val Cys Ala Cys Gln Val Arg Ala
                165                 170                 175

Thr Gly Lys Met Tyr Ala Cys Lys Lys Leu Gln Lys Lys Arg Ile Lys
            180                 185                 190

Lys Arg Lys Gly Glu Ala Met Ala Leu Asn Glu Lys Arg Ile Leu Glu
        195                 200                 205

Lys Val Gln Ser Arg Phe Val Val Ser Leu Ala Tyr Ala Tyr Glu Thr
    210                 215                 220

Lys Asp Ala Leu Cys Leu Val Leu Thr Ile Met Asn Gly Gly Asp Leu
225                 230                 235                 240

Lys Phe His Ile Tyr Asn Leu Gly Asn Pro Gly Phe Asp Glu Gln Arg
                245                 250                 255

Ala Val Phe Tyr Ala Ala Glu Leu Cys Cys Gly Leu Glu Asp Leu Gln
            260                 265                 270

Arg Glu Arg Ile Val Tyr Arg Asp Leu Lys Pro Glu Asn Ile Leu Leu
        275                 280                 285

Asp Asp Arg Gly His Ile Arg Ile Ser Asp Leu Gly Leu Ala Thr Glu
```

```
                290                 295                 300
Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
                325                 330                 335

Trp Trp Gly Leu Gly Cys Leu Ile Tyr Glu Met Ile Gln Gly His Ser
                340                 345                 350

Pro Phe Lys Lys Tyr Lys Glu Lys Val Lys Trp Glu Glu Val Asp Gln
                355                 360                 365

Arg Ile Lys Asn Asp Thr Glu Glu Tyr Ser Glu Lys Phe Ser Glu Asp
        370                 375                 380

Ala Lys Ser Ile Cys Arg Met Pro His Ala Val Tyr Cys Lys Asp Val
385                 390                 395                 400

Leu Asp Ile Glu Gln Phe Ser Ala Val Lys Gly Ile Tyr Leu Asp Thr
                405                 410                 415

Ala Asp Glu Asp Phe Tyr Ala Arg Phe Ala Thr Gly Cys Val Ser Ile
                420                 425                 430

Pro Trp Gln Asn Glu Gly Cys Leu Thr Met Val Pro Ser Glu Lys Glu
        435                 440                 445

Val Glu Pro Lys Gln Cys
    450

<210> SEQ ID NO 7
<211> LENGTH: 2113
<212> TYPE: DNA
<213> ORGANISM: Homo sapiens

<400> SEQUENCE: 7
gcagccgccg cggtcgggct gcccccctccc ctcgccccga ccgctcccct gctggtgagg      60
gcctgcgcag gcggcggcgg cggcgcccttt ggtggcagtg gtggcggcgg agcagcctcc     120
cgggatcgtg tctggagctc gaggagaggg tagtgcccgg cgagctatgc acggggggcgg   180
cggcgtctcc tcctgttccg cctcctcagt ctcctcggtc tcgcagaatc cgccggcggc   240
ggcggcgcca ggacatggag ctcgagaaca tcgtggccaa ctcgctgctg ctgaaagcgc   300
gtcaaggagg atatggcaaa aaaagtggtc gtagtaaaaa atggaaggag atactgacac   360
tgcctcctgt cagccagtgc agtgagctta gacattccat tgaaaaggat tatagcagtc   420
tttgtgacaa gcaaccgata ggaagacgtc tcttcaggca gttctgtgat accaaaccca   480
ctctaaagag gcacattgaa ttcttggatg cagtggcaga atgaagtt gccgatgatg   540
aggaccgaag tgattgtgga ctgtcaatct tagatagatt cttcaatgat aagttggcag   600
cccctttacc agaaatacct ccagatgttg tgacagaatg tagattggga ctgaaggagg   660
agaacccttc caaaaaagcc tttgaggaat gtactagagt tgcccataac tacctaagag   720
gggaaccatt tgaagaatac caagaaagct catattttc tcagtttta caatggaaat   780
ggctggaaag gcaacccgta acaaagaaca catttagaca ttcagagtt ctaggaaaag   840
gcggatttgg agaggtttgc gcctgtcaag tgcgagccac aggaaaaatg tatgcctgca   900
aaagctaca aaaaaaaga ataaagaaga ggaaaggtga agctatggct ctaaatgaga    960
aaagaattct ggagaaagtg caaagtagat cgtagttag tttagcctac gcttatgaaa   1020
ccaaagatgc cttgtgcttg gtgctccacca ttatgaatgg aggggatttg aagtttcaca  1080
tttacaacct gggcaatccc ggctttgatg agcagagagc cgttttctat gctgcagagc  1140
tgtgttgcgg cttggaagat ttacagaggg aaagaattgt atacagagac ttgaagcctg  1200
```

```
agaatattct ccttgatgat cgtggacaca tccggatttc agacctcggt ttggccacag    1260
agatcccaga aggacagagg gttcgaggaa gagttggaac agtcggctac atggcacctg    1320
aagttgtcaa taatgaaaag tatacgttta gtcccgattg gtggggactt ggctgtctga    1380
tctatgaaat gattcaggga cattctccat tcaaaaaata caaagagaaa gtcaaatggg    1440
aggaggtcga tcaaagaatc aagaatgata ccgaggagta ttctgagaag ttttcagagg    1500
atgccaaatc tatctgcagg atgttactca ccaagaatcc aagcaagcgg gtgggctgca    1560
ggggcgaggg agcggctggg gtgaagcagc accccgtgtt caaggacatc aacttcagga    1620
ggctggaggc aaacatgctg gagcccccct tctgtcctga tcctcatgcc gtttactgta    1680
aggacgtcct ggatatcgag cagttctcgg cggtgaaagg gatctacctg acaccgcag    1740 atgaagactt ctatgctcgg tttgctaccg ggtgtgtctc catcccctgg cagaatgaga    1800
tgatcgaatc cgggtgtttc aaagacatca acaaaagtga aagtgaggaa gctttgccat    1860
tagatctaga caagaacata catacccgg tttccagacc aaacagaggc ttcttctata    1920
gactcttcag aagagggggc tgcctgacca tggtccccag tgagaaggaa gtggaaccca    1980
agcaatgctg agcaccccgg tgcggaccac agagcagacc ctggcgccag aaggagcat    2040 gtgttagcgt ctcgtcccac ctggaattgt aataaataca tctaaataaa acatgccttg    2100
ggagtgtaca gac                                                      2113

<210> SEQ ID NO 8
<211> LENGTH: 2017
<212> TYPE: DNA
<213> ORGANISM: Homo sapiens

<400> SEQUENCE: 8
gcagccgccg cggtcgggct gcccccctccc ctcgccccga ccgctcccct gctggtgagg      60
gcctgcgcag gcggcggcgg cggcgcccctt ggtggcagtg gtggcggcgg agcagcctcc     120
cgggatcgtg tctggagctc gaggagaggg tagtgcccgg cgagctatgc acgggggcgg     180
cggcgtctcc tcctgttccg cctcctcagt ctcctcggtc tcgcagaatc cgccggcggc     240
ggcggcgcca ggacatggag ctcgagaaca tcgtggccaa ctcgctgctg ctgaaagcgc     300
gtcaagaaaa ggattatagc agtctttgtg acaagcaacc gataggaaga cgtctcttca     360
ggcagttctg tgataccaaa cccactctaa agaggcacat tgaattcttg gatgcagtgg     420
cagaatatga agttgccgat gatgaggacc gaagtgattg ggactgtca atcttagata     480 gattcttcaa tgataagttg gcagccccctt taccagaaat acctccagat gttgtgacag     540
aatgtagatt gggactgaag gaggagaacc cttccaaaaa agcctttgag gaatgtacta     600
gagttgccca taactaccta agaggggaac catttgaaga ataccaagaa agctcatatt     660
tttctcagtt tttacaatgg aaatggctgg aaaggcaacc cgtaacaaag aacacattta     720
gacattacag agttctagga aaaggcggat tggagaggtt ttgcgcctgt caagtgcgag     780
ccacaggaaa aatgtatgcc tgcaaaaagc tacaaaaaaa aagaataaag aagaggaaag     840
gtgaagctat ggctctaaat gagaaaagaa ttctggagaa agtgcaaagt agattcgtag     900
ttagtttagc ctacgcttat gaaaccaaag atgccttgtg cttggtgctc accattatga     960
atggagggga tttgaagttt cacatttaca acctgggcaa tcccggcttt gatgagcaga    1020
gagccgtttt ctatgctgca gagctgtgtt gcggcttgga agatttacag agggaaagaa    1080
ttgtatacag agacttgaag cctgagaata ttctccttga tgatcgtgga cacatccgga    1140
```

| | |
|---|---|
| tttcagacct cggtttggcc acagagatcc cagaaggaca gagggttcga ggaagagttg | 1200 |
| gaacagtcgg ctacatggca cctgaagttg tcaataatga aaagtatacg tttagtcccg | 1260 |
| attggtgggg acttggctgt ctgatctatg aaatgattca gggacattct ccattcaaaa | 1320 |
| aatacaaaga gaaagtcaaa tgggaggagg tcgatcaaag aatcaagaat gataccgagg | 1380 |
| agtattctga gaagttttca gaggatgcca aatctatctg caggatgtta ctcaccaaga | 1440 |
| atccaagcaa gcggctgggc tgcagggggcg agggagcggc tggggtgaag cagcaccccg | 1500 |
| tgttcaagga catcaacttc aggaggctgg aggcaaacat gctggagccc cctttctgtc | 1560 |
| ctgatcctca tgccgtttac tgtaaggacg tcctggatat cgagcagttc tcggcggtga | 1620 |
| aagggatcta cctggacacc gcagatgaag acttctatgc tcggtttgct accgggtgtg | 1680 |
| tctccatccc ctggcagaat gagatgatcg aatccgggtg tttcaaagac atcaacaaaa | 1740 |
| gtgaaagtga ggaagctttg ccattagatc tagacaagaa catacatacc ccggtttcca | 1800 |
| gaccaaacag aggcttcttc tatagactct tcagaagagg gggctgcctg accatggtcc | 1860 |
| ccagtgagaa ggaagtggaa cccaagcaat gctgagcacc ccggtgcgga ccacagagca | 1920 |
| gaccctggcg ccaggaagga gcatgtgtta gcgtctcgtc ccacctggaa ttgtaataaa | 1980 |
| tacatctaaa taaaacatgc cttgggagtg tacagac | 2017 |

<210> SEQ ID NO 9
<211> LENGTH: 1975
<212> TYPE: DNA
<213> ORGANISM: Homo sapiens

<400> SEQUENCE: 9

| | |
|---|---|
| gcagccgccg cggtcgggct gccccctccc ctcgccccga ccgctcccct gctggtgagg | 60 |
| gcctgcgcag gcggcggcgg cggcgccctt ggtggcagtg gtggcggcgg agcagcctcc | 120 |
| cgggatcgtg tctggagctc gaggagaggg tagtgcccgg cgagctatgc acggggggcgg | 180 |
| cggcgtctcc tcctgttccg cctcctcagt ctcctcggtc tcgcagaatc cgccggcggc | 240 |
| ggcggcgcca ggacatggag ctcgagaaca tcgtggccaa ctcgctgctg ctgaaagcgc | 300 |
| gtcaaggagg atatgcaaa aaagtggtc gtagtaaaaa atggaaggag atactgacac | 360 |
| tgcctcctgt cagccagtgc agtgagctta gacattccat tgaaaaggat tatagcagtc | 420 |
| tttgtgacaa gcaaccgata ggaagacgtc tcttcaggca gttctgtgat accaaaccca | 480 |
| ctctaaagag gcacattgaa ttcttggatg cagtggcaga atatgaagtt gccgatgatg | 540 |
| aggaccgaag tgattgtgga ctgtcaatct tagatagatt cttcaatgat aagttggcag | 600 |
| cccctttacc agaaatacct ccagatgttg tgacagaatg tagattggga ctgaaggagg | 660 |
| agaacccttc caaaaaagcc tttgaggaat gtactagagt tgcccataac tacctaagag | 720 |
| gggaaccatt tgaagaatac caagaaagct catattttc tcagtttta caatggaaat | 780 |
| ggctggaaag gcaacccgta acaaagaaca catttagaca ttacagagtt ctaggaaaag | 840 |
| gcggatttgg agaggtttgc gcctgtcaag tgcgagccac aggaaaaatg tatgcctgca | 900 |
| aaagctaca aaaaaaaaga ataagaaga ggaaaggtga agctatggct ctaaatgaga | 960 |
| aaagaattct ggagaaagtg caaagtgat tcgtagttag tttagcctac gcttatgaaa | 1020 |
| ccaaagatgc cttgtgcttg gtgctcacca ttatgaatgg agggatttg aagtttcaca | 1080 |
| tttacaacct gggcaatccc ggctttgatg agcagagagc cgttttctat gctgcagagc | 1140 |
| tgtgttgcgc cttggaagat ttacagaggg aaagaattgt atacagagac ttgaagcctg | 1200 |
| agaatattct ccttgatgat cgtggacaca tccggatttc agacctcggt ttggccacag | 1260 |

-continued

| | |
|---|---|
| agatcccaga aggacagagg gttcgaggaa gagttggaac agtcggctac atggcacctg | 1320 |
| aagttgtcaa taatgaaaag tatacgttta gtcccgattg gtggggactt ggctgtctga | 1380 |
| tctatgaaat gattcaggga cattctccat tcaaaaaata caaagagaaa gtcaaatggg | 1440 |
| aggaggtcga tcaaagaatc aagaatgata ccgaggagta ttctgagaag ttttcagagg | 1500 |
| atgccaaatc tatctgcagg atgttactca ccaagaatcc aagcaagcgg ctgggctgca | 1560 |
| ggggcgaggg agcggctggg gtgaagcagc accccgtgtt caaggacatc aacttcagga | 1620 |
| ggctggaggc aaacatgctg agccccctt tctgtcctga tcctcatgcc gtttactgta | 1680 |
| aggacgtcct ggatatcgag cagttctcgg cggtgaaagg gatctacctg acaccgcag | 1740 |
| atgaagactt ctatgctcgg tttgctaccg ggtgtgtctc catcccctgg cagaatgagg | 1800 |
| gctgcctgac catggtcccc agtgagaagg aagtggaacc caagcaatgc tgagcacccc | 1860 |
| ggtgcggacc acagagcaga ccctggcgcc aggaaggagc atgtgttagc gtctcgtccc | 1920 |
| acctggaatt gtaataaata catctaaata aacatgcct tgggagtgta cagac | 1975 |

<210> SEQ ID NO 10
<211> LENGTH: 1879
<212> TYPE: DNA
<213> ORGANISM: Homo sapiens

<400> SEQUENCE: 10

| | |
|---|---|
| gcagccgccg cggtcgggct gcccctccc ctcgccccga ccgctcccct gctggtgagg | 60 |
| gcctgcgcag gcggcggcgg cggcgccctt ggtggcagtg gtggcggcgg agcagcctcc | 120 |
| cgggatcgtg tctggagctc gaggagaggg tagtgcccgg cgagctatgc acgggggcgg | 180 |
| cggcgtctcc tcctgttccg cctcctcagt ctcctcggtc tcgcagaatc cgccggcggc | 240 |
| ggcggcgcca ggacatggag ctcgagaaca tcgtggccaa ctcgctgctg ctgaaagcgc | 300 |
| gtcaagaaaa ggattatagc agtctttgtg acaagcaacc gataggaaga cgtctcttca | 360 |
| ggcagttctg tgataccaaa cccactctaa agaggcacat tgaattcttg gatgcagtgg | 420 |
| cagaatatga agttgccgat gatgaggacc gaagtgattg tggactgtca atcttagata | 480 |
| gattcttcaa tgataagttg gcagccccctt taccagaaat acctccagat gttgtgacag | 540 |
| aatgtagatt gggactgaag gaggagaacc cttccaaaaa agcctttgag gaatgtacta | 600 |
| gagttgccca taactaccta agaggggaac catttgaaga ataccaagaa agctcatatt | 660 |
| tttctcagtt tttacaatgg aaatggctgg aaaggcaacc cgtaacaaag aacacattta | 720 |
| gacattacag agttctagga aaaggcggat ttggagaggt ttgcgcctgt caagtgcgag | 780 |
| ccacaggaaa aatgtatgcc tgcaaaaagc tacaaaaaaa agaataaag aagaggaaag | 840 |
| gtgaagctat ggctctaaat gagaaaagaa ttctggagaa agtgcaaagt agattcgtag | 900 |
| ttagtttagc ctacgcttat gaaaccaaag atgccttgtg cttggtgctc accattatga | 960 |
| atgggaggga tttgaagttt cacatttaca acctgggcaa tccggcttt gatgagcaga | 1020 |
| gagccgtttt ctatgctgca gagctgtgtt gcggcttgga agatttacag agggaaagaa | 1080 |
| ttgtatacag agacttgaag cctgagaata ttctccttga tgatcgtgga cacatccgga | 1140 |
| tttcagacct cggtttggcc acagagatcc cagaaggaca gagggttcga ggaagagttg | 1200 |
| gaacagtcgg ctacatggca cctgaagttg tcaataatga aaagtatacg tttagtcccg | 1260 |
| attggtgggg acttggctgt ctgatctatg aaatgattca gggacattct ccattcaaaa | 1320 |
| aatacaaaga gaaagtcaaa tgggaggagg tcgatcaaag aatcaagaat gataccgagg | 1380 |

| agtattctga gaagttttca gaggatgcca aatctatctg caggatgtta ctcaccaaga | 1440 |
| atccaagcaa gcggctgggc tgcaggggcg agggagcggc tggggtgaag cagcaccccg | 1500 |
| tgttcaagga catcaacttc aggaggctgg aggcaaacat gctggagccc cctttctgtc | 1560 |
| ctgatcctca tgccgtttac tgtaaggacg tcctggatat cgagcagttc tcggcggtga | 1620 |
| aagggatcta cctggacacc gcagatgaag acttctatgc tcggtttgct accgggtgtg | 1680 |
| tctccatccc ctggcagaat gagggctgcc tgaccatggt ccccagtgag aaggaagtgg | 1740 |
| aacccaagca atgctgagca ccccggtgcg gaccacagag cagaccctgg cgccaggaag | 1800 |
| gagcatgtgt tagcgtctcg tcccacctgg aattgtaata aatacatcta aataaaacat | 1860 |
| gccttgggag tgtacagac | 1879 |

<210> SEQ ID NO 11
<211> LENGTH: 1420
<212> TYPE: DNA
<213> ORGANISM: Homo sapiens

<400> SEQUENCE: 11

| atggagctcg agaacatcgt ggccaactcg ctgctgctga aagcgcgtca aggaggatat | 60 |
| ggcaaaaaaa gtggtcgtag taaaaaatgg aaggagatac tgacactgcc tcctgtcagc | 120 |
| cagtgcagtg agcttagaca ttccattgaa aaggattata gcagtctttg tgacaagcaa | 180 |
| ccgataggaa gacgtctctt caggcagttc tgtgatacca aacccactct aaagaggcac | 240 |
| attgaattct ggatgcagt ggcagaatat gaagttgccg atgatgagga ccgaagtgat | 300 |
| tgtggactgt caatcttaga tagattcttc aatgataagt tggcagcccc tttaccagaa | 360 |
| atacctccag atgttgtgac agaatgtaga ttgggactga aggaggagaa cccttccaaa | 420 |
| aaagcctttg aggaatgtac tagagttgcc cataactacc taagagggga accatttgaa | 480 |
| gaataccaag aaagctcata tttttctcag tttttacaat ggaaatggct ggaaaggcaa | 540 |
| cccgtaacaa agaacacatt tagacattac agagttctag aaaaggcgg atttggagag | 600 |
| gtttgcgcct gtcaagtgcg agccacagga aaatgtatg cctgcaaaaa gctacaaaaa | 660 |
| aaagaataa agaagaggaa aggtgaagct atggctctaa atgagaaaag aattctggag | 720 |
| aaagtgcaaa gtagattcgt agttagttta gcctacgctt atgaaaccaa agatgccttg | 780 |
| tgcttggtgc tcaccattat gaatggaggg gatttgaagt ttcacattta caacctgggc | 840 |
| aatcccggct tgatgagca gagagccgtt ttctatgctg cagagctgtg ttgcggcttg | 900 |
| gaagatttac agagggaaag aattgtatac agagacttga gcctgagaa tattctcctt | 960 |
| gatgatcgtg gacacatccg gatttcagac ctcggtttgg ccacagagat cccagaagga | 1020 |
| cagagggttc gaggaagagt tggaacagtc ggctacatgg cacctgaagt tgtcaataat | 1080 |
| gaaaagtata cgtttagtcc cgattggtgg ggacttggct gtctgatcta tgaaatgatt | 1140 |
| cagggacatt ctccattcaa aaaatacaaa gagaaagtca atgggagga ggtcgatcaa | 1200 |
| agaatcaaga tgataccga ggagtattct gagaagtttt cagaggatgc caaatctatc | 1260 |
| tgcaggatgc ctcatgccgt ttactgtacc tcatgccgtt tactgtaatg aagacttcta | 1320 |
| tgctcggttt gctaccgggt gtgtctccat cccctggcag aatgagggct gcctgaccat | 1380 |
| ggtcccagt gagaaggaag tggaacccaa gcaatgctga | 1420 |

<210> SEQ ID NO 12
<211> LENGTH: 1305
<212> TYPE: DNA
<213> ORGANISM: Homo sapiens

<400> SEQUENCE: 12

```
atggagctcg agaacatcgt ggccaactcg ctgctgctga agcgcgtca agaaaaggat    60
tatagcagtc tttgtgacaa gcaaccgata ggaagacgtc tcttcaggca gttctgtgat   120
accaaaccca ctctaaagag gcacattgaa ttcttggatg cagtggcaga atatgaagtt   180
gccgatgatg aggaccgaag tgattgtgga ctgtcaatct tagatagatt cttcaatgat   240
aagttggcag cccctttacc agaaatacct ccagatgttg tgacagaatg tagattggga   300
ctgaaggagg agaacccttc caaaaaagcc tttgaggaat gtactagagt tgcccataac   360
tacctaagag gggaaccatt tgaagaatac caagaaagct catatttttc tcagttttta   420
caatggaaat ggctggaaag gcaacccgta acaagaaca catttagaca ttacagagtt   480
ctaggaaaag gcggatttgg agaggtttgc gcctgtcaag tgcgagccac aggaaaaatg   540
tatgcctgca aaaagctaca aaaaaaaga ataagaaga ggaaggtga agctatggct    600
ctaaatgaga aagaattct ggagaaagtg caaagtagat tcatagttag tttagcctac   660
gcttatgaaa ccaaagatgc cttgtgcttg gtgctcacca ttatgaatgg aggggatttg   720
aagtttcaca tttacaacct gggcaatccc ggctttgatg agcagagagc cgttttctat   780
gctgcagagc tgtgttgcgg cttggaagat ttacagaggg aaagaattgt atacagagac   840
ttgaagcctg agaatattct ccttgatgat cgtggacaca tccggatttc agacctcggt   900
ttggccacag agatcccaga aggacagagg gttcgaggaa gagttggaac agtcggctac   960
atggcacctg aagttgtcaa taatgaaaag tatacgttta gtcccgattg gtggggactt  1020
ggctgtctga tctatgaaat gattcaggga cattctccat tcaaaaaata caaagagaaa  1080
gtcaaatggg aggaggtcga tcaaagaatc aagaatgata ccgaggagta ttctgagaag  1140
ttttcagagg atgccaaatc tatctgcagg atgcctcatg ccgtttactg taatgaagac  1200
ttctatgctc ggtttgctac cgggtgtgtc tccatcccct ggcagaatga gggctgcctg  1260
accatggtcc ccagtgagaa ggaagtggaa cccaagcaat gctga              1305
```

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: GRK4 Primer

<400> SEQUENCE: 13

```
aaaaggatta tagcagtctt tgtgacaa                                       28
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: GRK4 Primer

<400> SEQUENCE: 14

```
cactgcatcc aagaattcaa tgtgcctc                                       28
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: GRK4 Primer

```
<400> SEQUENCE: 15
ctaatggtta tgtatttggt t                                              21

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: GRK4 Primer

<400> SEQUENCE: 16
atgcagggct cagcatga                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: GRK4 Primer

<400> SEQUENCE: 17
aggtggacat aaacctcc                                                  18

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: GRK4 Primer

<400> SEQUENCE: 18
caaacaatgc acagtgaag                                                 19

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: GRK4 Primer

<400> SEQUENCE: 19
cctcatgccg tttactgtaa ggacgtcc                                       28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: GRK4 Primer

<400> SEQUENCE: 20
ctcattctgc caggggatgg agacacac                                       28

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: GRK4 Primer

<400> SEQUENCE: 21
gcatcagccg tgtgcct                                                   17

<210> SEQ ID NO 22
<211> LENGTH: 18
```

```
<212> TYPE: DNA
<213> ORGANISM: Artificial Sequence
<220> FEATURE:
<223> OTHER INFORMATION: Description of Artificial Sequence: GRK4 Primer

<400> SEQUENCE: 22
gtgcagaagg tctgtaca                                                  18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 23
cctgaagaga cgtcttccta                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 24
cctgaagaga agtcttccta                                                20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 25
ccaaaaaagc ctttgagga                                                 19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 26
ccaaaaaagt ctttgagga                                                 19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 27
agtagattcg tagtaagtg                                                 19

<210> SEQ ID NO 28
<211> LENGTH: 19
<212> TYPE: DNA
<213> ORGANISM: Artificial Sequence
```

<220> FEATURE:
<223> OTHER INFORMATION: Description of Artificial Sequence: GRK4 allele
      specific oligonucleotide

<400> SEQUENCE: 28
agtagattca tagtaagtg                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 29
agttctcggc ggtgaaagg                                                19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 30
agttctcggt ggtgaaagg                                                19

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 31
tgttgtagga ctgcctga                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: GRK4 allele
      specific oligonucleotide

<400> SEQUENCE: 32
tgttgtaggg ctgcctga                                                 18

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 33
cacgatgttc tcgagctcca t                                             21

<210> SEQ ID NO 34
<211> LENGTH: 18
<212> TYPE: DNA
<213> ORGANISM: Artificial Sequence
<220> FEATURE:

-continued

```
<223> OTHER INFORMATION: Description of Artificial Sequence: antisense
      oligonucleotide

<400> SEQUENCE: 34
ctccatgtcc tggcgccg                                                      18
```

G PROTEIN-RELATED KINASE MUTANTS IN ESSENTIAL HYPERTENSION

CROSS-REFERENCE TO RELATED APPLICATIONS

The present application is a continuation of U.S. application Ser. No. 10/677,983, filed on Oct. 2, 2003, which is a divisional of U.S. application Ser. No. 09/614,748, now U.S. Pat. No. 6,660,474, filed on Jul. 12, 2000, which is a continuation of International Application No. PCT/US99/00663, filed on Jan. 12, 1999, which claims the benefit of U.S. Provisional Application No. 60/071,199, filed on Jan. 12, 1998, and U.S. Provisional Application No. 60/098,279, filed on Aug. 28, 1998, the disclosures of which are incorporated by reference herein.

STATEMENT REGARDING FEDERALLY SPONSORED RESEARCH

The work leading to the invention described herein was funded in part by National Institute of Health grant NIH: DK 39308.HL 23081. Therefore, the Government may have certain rights in the invention.

FIELD OF THE INVENTION

The present invention relates to essential hypertension, and more particularly to the use of genetic markers in diagnostic and therapeutic approaches to this disease.

BACKGROUND OF THE INVENTION

Essential hypertension, or high blood pressure of unknown cause, is a disease that affects 25-30% of Caucasians in The United States. Left untreated, hypertension leads to heart disease, stroke, myocardial infarction, and end-stage kidney disease. Since hypertension patients do not generally feel sick, it is often undiagnosed and left untreated until end organ failure has begun. Thus hypertension is the leading cause of cardiovascular morbidity and mortality in humans. Many hypertensives are salt sensitive in that a high salt diet will cause an elevation in blood pressure or exacerbate an already elevated blood pressure. Finding a measure for the propensity to develop high blood pressure could have a significant impact on reducing cardiovascular disease.

It has been estimated that genetic factors account for 30-40% of blood pressure variability in humans (Ward, In *Hypertension: Pathophysiology, Diagnosis and Management*, Laragh J H. and Brenner B M eds., (Raven Press, Ltd., New York, N.Y.), 81-100 (1990).) However, other estimates have suggested that genetic heritability of hypertension may be as high as 80% with 40% accounted for by one major gene (Cavalli, et al., in *The Genetics of Human Population*, (WH Freeman Co., South San Francisco, Calif.) 534-536 (1971)). The single major gene could affect blood pressure to such a significant extent that it would dominate many other genes that play a minor role in blood pressure control.

The central role of the kidneys in the genesis and maintenance of hypertension has been well established. When normal kidneys are transplanted into hypertensive rats, their blood pressure is normalized. On the other hand, when kidneys from hypertensive rats are transplanted into normotensive rats, they develop hypertension. Thus hypertension seems to follow the kidneys. It is also known that most human genetic forms of hypertension are associated with enhanced reabsorption of sodium in the kidney. Although there are many hormonal systems that regulate renal sodium excretion and blood pressure, the renal paracrine function of dopamine is well established as an important mechanism in long-term blood pressure regulation. The increased avidity of the renal proximal tubule for sodium in hypertension may be caused by defective renal paracrine action of dopamine. Dopamine causes a decrease in sodium reabsorption. Thus a defect in the action of dopamine would lead to an increase in sodium reabsorption and hypertension.

Dopamine exerts its actions via a class of cell surface receptors that belong to the rhodopsin-like family of G protein coupled receptors; these receptors have in common 7 trans-membrane domains. The dopamine receptors in the CNS and some endocrine organs are grouped into two major classes, the D1-like and the D2-like receptors. In the kidney and other organs outside the CNS, the D1-like receptors have been called DA1 receptors while the D2-like receptors have been called DA2 receptors. These distinctions are probably no longer necessary since no dopamine receptor is expressed exclusively inside or outside the CNS. However, there is differential regulation of the D1 receptor in neural and renal tissue. The two exons of the D1 receptor gene are transcribed in neural tissue while only the second exon is transcribed in renal tissue. The differential expression of the short and long D1 transcript may be due to tissue-specific expression of an activator protein driving transcription from a promoter at the 5' non-coding region of the D1 receptor gene. Each of the D2-like dopamine receptor subtypes has several isoforms. However, no particular isoform is specifically expressed in peripheral tissues. See, Jose et. al., Pharmac. Ther. 80:149-182 (1998).

Two D1-like receptors are expressed in mammals: the D1 and D5 receptors which are known as D1A and D1B in rodents, respectively. Two additional D1-like receptors, D1C and D1D, are expressed in non-mammalian species. The D1-like receptors are linked to stimulation of adenylyl cyclase. The D1A receptor also stimulates phospholipase C activity, but this is secondary to stimulation of adenylyl cyclase. There seems to be a D1-like receptor, that is, as yet uncloned, linked to phospholipase C (PLC), through a pertussis toxin insensitive G-protein, Gq, that is distinct from the D1 and D5 receptor (Jose et al., Pharmac. Ther 80:149-182 (1998)). Three D2-like receptors are expressed in mammals: the D2, D3, and D4 receptors. The D2-like receptors are linked to inhibition of adenylyl cyclase and Ca2+ channels. The D2-like receptors also stimulate K+ channels although the D2 and D3 receptors have been reported to decrease voltage dependent potassium current in NG108-15 cells. Both the D2 and D3 receptors present in presynaptic nerves may also serve to decrease the release of both dopamine and norepinephrine.

All the mammalian dopamine receptors, initially cloned from the brain, have been found to be expressed in the kidney and urinary tract. Dopamine receptor subtypes are differentially expressed along the renal vasculature, the glomerulus, and the renal tubule where they regulate renal hemodynamics and electrolyte and water transport as well as renin secretion. Exogenous dopamine, at low doses, decreases renal vascular resistance and increases renal blood flow but with variable effects on glomerular filtration rate. Additional renal effects include an increase in solute and water excretion caused by hemodynamic and tubular mechanisms. The ability of renal proximal tubules to produce dopamine and the presence of receptors in these tubules suggest that dopamine can act in an autocrine or paracrine fashion. Endogenous renal dopamine increases solute and water excretion by actions at several nephron segments (proximal tubule, medullary thick ascending limb of Henle (mTAL), cortical collecting duct (CCD)). The magnitude of the inhibitory effect of dopamine on each nephron segment is modest but the multiple sites of action along the nephron cause impressive increases in solute and water excretion. The renal effects of dopamine are most apparent under conditions of solute (e.g., sodium, phosphate) or protein load. D1-like receptors, probably of the D1 subtype, vasodilate the kidney, inhibit sodium transport in proximal tubules by inhibition of sodium/hydrogen exchanger activity at the luminal membrane and sodium/potassium ATPase activity at the basolateral membrane. D1-like receptors also decrease sodium transport in the mTAL and in the CCD. The major functional D1-like receptor in the kidney is the D1 receptor. Presynaptic D2-like receptors are also vasodilatory. Postsynaptic D2-like receptors, by themselves, stimulate renal proximal sodium transport and inhibit the action of vasopressin at the CCD. However, in concert with D1-like receptors, postsynaptic D2-like receptors may act synergistically to inhibit sodium transport in the renal proximal tubule. The major D2-like receptor in the proximal tubule is the D3 receptor while the major D2-like receptor in the CCD is the D4 receptor. The ability of postsynaptic D2-like receptors, probably of the D3 subtype, to inhibit renin secretion may counteract the stimulatory effect of D1-like receptors on renin secretion and contribute to their synergistic action to increase sodium excretion in sodium replete states (Jose et al., supra).

In conclusion, although many years of intensive effort have revealed much about the etiology of essential hypertension, a single major gene that controls blood pressure has not been found. Thus the discovery of a major gene associated with blood pressure regulation would be important for understanding the mechanisms causing essential hypertension and lead to important new diagnostics and therapeutics.

SUMMARY OF THE INVENTION

Kinases are enzymes that catalyze the addition of a phosphate group onto proteins. G protein-coupled receptor kinases (GRKs) are a family of protein kinases that phosphorylate G protein-coupled receptor proteins on serine and threonine residues. GRKs, along with other proteins called arrestins, mediate homologous desensitization of hormonal responses. See, Premont, et al., FASEB J. 9:175-162 (1995). Six GRKs have been identified, i.e., GRK1-GRK6. See, Premont, et al., supra.; Palczewski, Protein Sci. 3:1355-1361 (1994); and Inglese, et al., J. Biol. Chem. 268:23735-23738 (1993). GRK4 had been the least well-understood member of the GRK family. Premont et al., J. Biol. Chem. 271:6403-6410 (1996), determined its presence substantially in testis, and thus is the least distributed of any GRK except GRK1. Although the Premont publication acknowledges that it was not known as to which specific type of testis cell expressed GRK4, it speculates that GRK4 could bind to any one of a number of receptors, including the LH/CG receptor, the gonadotropin-releasing hormone receptor, and follicle-stimulating hormone receptor and a variety of olfactory receptors. Later, Gros, J. Clin. Invest. 99(9):2087-2093 (1997), implicated GRK2 activity in reduced adenylyl cyclase activation in lymphocytes from hypertensive individuals. Gros also observed that the increase in GRK activity was associated exclusively with an increase in GRK2 expression, and that the activity of other GRKs was not altered.

Applicants have made several important discoveries. First, GRK4 isoform expression occurs to a significant extent in the kidney, and specifically in renal proximal tubule and cortical collecting duct cells. Second, Applicants discovered that several known polymorphic forms of GRK4, and three more previously unknown polymorphs, are prevalent in hypertensive individuals. Third, the D1 receptor/adenylyl cyclase coupling defect in renal proximal tubule cells known to be associated with essential hypertensive individuals is associated with but not limited to hyperphosphorylation of the D1 receptor.

Commercial embodiments of Applicants' invention fall into three primary areas, namely diagnostics, drug discovery and therapy. Accordingly, a first aspect of the present invention is directed to methods for identifying individuals predisposed to essential hypertension. The methods can be conducted using a sample of kidney cells that express a D1 receptor and GRK4, isolated from the individual, wherein the cells are assayed to determine the extent of post-translational modification of the D1 receptor, such as phosphorylation or palmitoylation, wherein a change in the post-translational modification of the receptor relative to cells isolated from a normotensive individual is indicative of predisposition to essential hypertension. Alternatively, a nucleic acid sample is isolated from the individual in order to analyze a GRK4 gene or fragment thereof to detect GRK4 associated with essential hypertension. Specific mutants that applicants have identified as being associated with essential hypertension include the following: R65L, A142V, A486V, the two double mutants R65L, A486V, and R65L, A142V, and the triple mutant R65L, A142V, A486V. Identifying yet other mutant GRK4s associated with essential hypertension can be conducted simply by analyzing GRK4 genes isolated from individuals diagnosed with essential hypertension, and analyzing the sequence of the GRK4 gene. The applicants further demonstrated that expression of these GRK4s in non-renal cells cause these non-renal cells to fail to "properly" (e.g., normally) transduce a dopaminergic signal.

A related aspect of the present invention is directed to isolated and purified nucleic acids encoding a GRK4 protein having an R65L, A142V double mutation, an R65L, A486V double mutation, or an R65L, A142V, A486V triple mutation. Oligonucleotides which specifically hybridize to GRK4 gene fragments containing the aforementioned mutations are also disclosed. Further disclosed are oligonucleotide primers, or primer pairs, which hybridize to fragments of the GRK4 gene containing a mutation associated with essential hypertension. Preferred primers which specifically hybridize to exon 3, 5, 8, 14 or 16 of a GRK4 gene and which is useful in amplifying DNA sequences including nucleotides 431-503 (exon 3), 594-697 (exon 5), 857-995 (exon 8), 1662-1798 (exon 14) or 1937-1991 (exon 16) of the GRK4 gene.

Another aspect of the present invention is related to various systems in which to test substances for anti-hypertensive activity by their ability to effect a change in GRK4 conformation and/or activity. These systems range from complexes between a GRK4 protein, e.g., wild-type or an isoform or mutant that is associated with essential hypertension, and an agent that causes a conformational change of the GRK4 protein upon interaction with an anti-hypertensive agent to be detected, to reconstituted systems containing GRK4 and a GRK4 substrate. Any system in which the interaction between GRK4 and a GRK4 substrate can be measured can be used to screen for potential anti-hypertensive agents. Thus, the systems range from cell-like parts such as an artificial membrane, e.g., lipid micelle, to whole cells. Preferred whole cells include cells transfected with a D1 receptor gene (or a functional fragment thereof) and a wild-type or mutant GRK4 gene, and immortalized human proximal tubule cells. Changes in GRK4 activity that occur in these various systems can be detected by measuring pertubations in cell activity such as any second messenger component or endpoint such as (but not limited to) cAMP generated by adenylyl cyclase, G protein activity, sodium transporter or pump activity, and post-translational modifications such as phosphorylation and palmitoylation. In vivo systems such as transgenic animals containing a transgene encoding a GRK4 protein associated with essential hypertension, wherein the transgene is expressed in renal cells to cause the transgenic animal to exhibit a state of essential hypertension, are also disclosed.

Yet another aspect of the present invention is directed to methods for decreasing sodium transport (increasing natriuresis) in renal proximal tubule cells in vitro or in vivo. The basic objectives of these therapeutic applications are to change GRK4 activity. One preferred method involves administration of an agent or agents that reduce or prevent expression of the GRK4s in renal cells of the hypertensive individual. GRK4 mRNA or DNA can be attacked with oligonucleotides such as antisense RNA or dominant negative mutants that prevent transcription or translation. Ribozymes that cleave GRK4 mRNA or pre-mRNA are also useful. Other therapeutic applications include drugs that alter e.g., inhibit or enhance the activity of GRK4 (either inhibition or stimulation).

Without being bound by any particular theory of operation, Applicants believe that a renal defect is responsible for a certain portion of hypertension in human subjects, and that the GRK4 mutation either causes among other things, a direct or indirect ligand independent serine-hyperphosphorylation of the D1 receptor, resulting in its uncoupling from the G protein/effector complex. The result is that the natriuretic effect of dopamine is compromised and the kidney is unable to properly balance sodium and water, leading to sodium retention and elevated blood pressure. More specifically, renal proximal tubules obtained from human hypertensive subjects, but not from normotensive subjects, demonstrate a defective coupling of the dopamine D1 receptor with adenylyl cyclase. The defective coupling is associated with a ligand-independent phosphorylation of the D1 receptor. Applicants have discovered at least six mutations in G protein related kinase type 4 (GRK4) that regulate ligand-independent phosphorylation of the D1 receptor in hypertensive patients.

DETAILED DESCRIPTION

Figure 1:
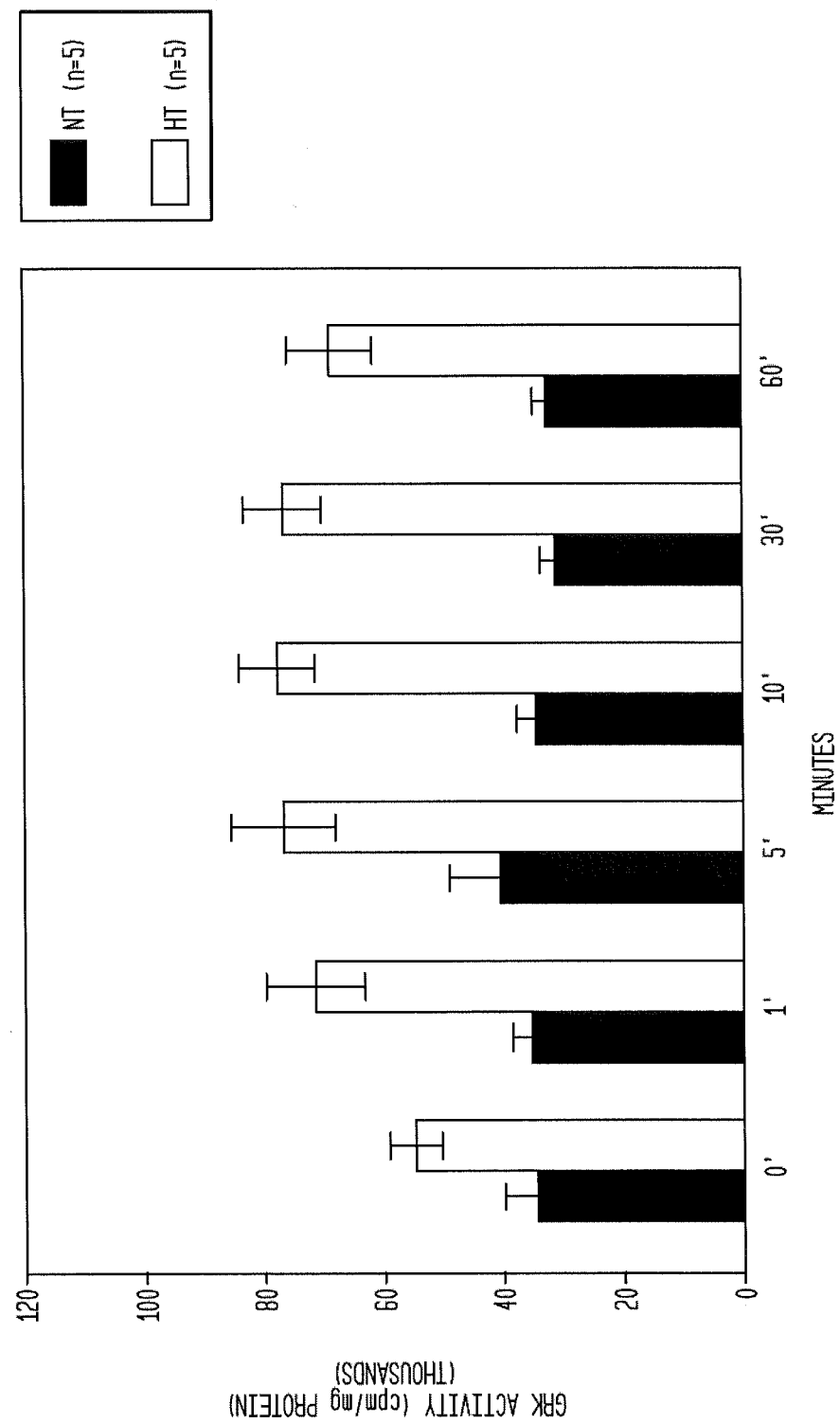
FIG. 1 is a graph that shows that a D1-like agonist stimulates GRK activity in renal proximal tubule cells from hypertensive but not from normotensive subjects.

The structure of the human GRK4 gene transcript undergoes extensive alternative splicing to generate four distinct forms of GRK4 mRNA that encode four forms of the GRK4 protein. The alternative splicing occurs at the amino- and/or carboxyl-terminal regions of GRK4, giving rise to the four isoforms.

GRK4 is originally reported in Ambrose, et al., Hum. Mol. Genet. 1:697-703 (1993), and then more extensively characterized in Premont et al., J. Biol. Chem. 271(11):6403-6410 (1996). Premont reports that GRK4 is highly abundant in testis only, GRK4 mRNA being present to a small extent in brain and skeletal muscle. The GRK4 gene, exclusive of promoter regions, spans approximately 75 kilobases (kDa), and is composed of 16 exons. The longest form of GRK4, with intact amino- and carboxyl-terminal alternative exon sequences, has been designated GRK4α. The deduced protein sequence contains 578 amino acids, with a predicted molecular mass of 66.5 kDa. The next shorter form, GRK4O, lacks only the amino-terminal alternative exon, which is composed of codons, and thus contains 546 amino acids having a molecular mass of 62 kDa. GRK4 gamma is the isoform lacking only the carboxyl-terminal alternative exon, which is 46 codons. Thus, this isoform contains 532 amino acids, and has a predicted molecular mass of 61.2 kDa. GRK4γ was formally called GRK4A. See Sallese et al., Biochem. Biophys. Res. Commun. 199:848-854 (1994). GRK4Δ contains 500 amino acids with a predicted molecular mass of 57.6 kDA, and is the shortest isoform. It lacks both alternative exons. GRK4L was originally designated IT11 and GRK4B. See Sallese et al., supra, and Ambrose, et al., supra. More recently, two additional isoforms have been discovered, namely: GRK4ε which lacks exons 13 and 15, contains 486 amino acids with a predicted molecular mass of 53.6 kDa, and GRK4ζ which lacks exons 2, 13 and 15, contains 454 amino acids with a predicted molecular mass of 49.9 kDa.

Five single nucleotide polymorphisms of GRK4 are also known, namely: R65L (CGT to CTT); A142V (GCC to GTC); V247I (GTA to ATA); A486V (GCG to GTG) and D562G (GAC to GGC). See Premont, et al., supra. Applicants have discovered that the R61L, the A142V and the A486V polymorphisms are associated with essential hypertension. Applicants have also discovered three additional polymorphisms prevalent in hypertensive individuals, namely: the double mutants R65L, A142V and R65L, A486V; and the triple mutant R65L, A142V, A486V. Table 1 shows the amino acid and corresponding nucleotide sequences of the six GRK4 isoforms. Amino acids and corresponding nucleotides that are changed in the polymorphs associated with essential hypertension are shown in bold. The sequences of the 5' untranslated regions of the ε and ζ isoforms are not shown.

TABLE 1

| | | | | | | |
|---|---|---|---|---|---|---|
| MELENIVANS | LLLKARQGGY | GKKSGRSKKW | KEILTLPPVS | QCSELRHSIE | 50 | GRK4α |
| MELENIVANS | LLLKARQ--- | ---------- | ---------- | ---------E | | GRK4β |
| MELENIVANS | LLLKARQGGY | GKKSGRSKKW | KEILTLPPVS | QCSELRHSIE | | GRK4γ |
| MELENIVANS | LLLKARQ--- | ---------- | ---------- | ---------E | | GRK4δ |
| MELENIVANS | LLLKARQGGY | GKKSGRSKKW | KEILTLPPVS | QCSELRHSIE | | GRK4ε |

TABLE 1-continued

```
MELENIVANS LLLKARQ--- ---------- ---------- ---------E                      GRK4ζ

KDYSSLCDKQ PIGRRLFRQF CDTKPTLKRH IEFLDAVAEY EVADDEDRSD         100          GRK4α
KDYSSLCDKQ PIGRRLFRQF CDTKPTLKRH IEFLDAVAEY EVADDEDRSD                      GRK4β
KDYSSLCDKQ PIGRRLFRQF CDTKPTLKRH IEFLDAVAEY EVADDEDRSD                      GRK4γ
KDYSSLCDKQ PIGRRLFRQF CDTKPTLKRH IEFLDAVAEY EVADDEDRSD                      GRK4δ
KDYSSLCDKQ PIGRRLFRQF CDTKPTLKRH IEFLDAVAEY EVADDEDRSD                      GRK4ε
KDYSSLCDKQ PIGRRLFRQF CDTKPTLKRH IEFLDAVAEY EVADDEDRSD                      GRK4ζ

CGLSILDRFF NDKLAAPLPE IPPDVVTECR LGLKEENPSK KAFEECTRVA         150          GRK4α
CGLSILDRFF NDKLAAPLPE IPPDVVTECR LGLKEENPSK KAFEECTRVA                      GRK4β
CGLSILDRFF NDKLAAPLPE IPPDVVTECR LGLKEENPSK KAFEECTRVA                      GRK4γ
CGLSILDRFF NDKLAAPLPE IPPDVVTECR LGLKEENPSK KAFEECTRVA                      GRK4δ
CGLSILDRFF NDKLAAPLPE IPPDVVTECR LGLKEENPSK KAFEECTRVA                      GRK4ε
CGLSILDRFF NDKLAAPLPE IPPDVVTECR LGLKEENPSK KAFEECTRVA                      GRK4ζ

HNYLRGEPFE EYQESSYFSQ FLQWKWLERQ PVTKNTFRHY RVLGKGGFGE         200          GRK4α
HNYLRGEPFE EYQESSYFSQ FLQWKWLERQ PVTKNTFRHY RVLGKGGFGE                      GRK4β
HNYLRGEPFE EYQESSYFSQ FLQWKWLERQ PVTKNTFRHY RVLGKGGFGE                      GRK4γ
HNYLRGEPFE EYQESSYFSQ FLQWKWLERQ PVTKNTFRHY RVLGKGGFGE                      GRK4δ
HNYLRGEPFE EYQESSYFSQ FLQWKWLERQ PVTKNTFRHY RVLGKGGFGE                      GRK4ε
HNYLRGEPFE EYQESSYFSQ FLQWKWLERQ PVTKNTFRHY RVLGKGGFGE                      GRK4ζ

VCACQVRATG KMYACKKLQ  KRIKKRKGEA MALNEKRILE KVQSRFVVSL         250          GRK4α
VCACQVRATG KMYACKKLQ  KRIKKRKGEA MALNEKRILE KVQSRFVVSL                      GRK4β
VCACQVRATG KMYACKKLQ  KRIKKRKGEA MALNEKRILE KVQSRFVVSL                      GRK4γ
VCACQVRATG KMYACKKLQ  KRIKKRKGEA MALNEKRILE KVQSRFVVSL                      GRK4δ
VCACQVRATG KMYACKKLQK KRIKKRKGEA MALNEKRILE KVQSRFVVSL                      GRK4ε
VCACQVRATG KMYACKKLQ  KRIKKRKGEA MALNEKRILE KVQSRFVVSL                      GRK4ζ

AYAYETKDAL CLVLTIMNGG DLKFHIYNLG NPGFDEQRAV FYAAELCCGL         300          GRK4α
AYAYETKDAL CLVLTIMNGG DLKFHIYNLG NPGFDEQRAV FYAAELCCGL                      GRK4β
AYAYETKDAL CLVLTIMNGG DLKFHIYNLG NPGFDEQRAV FYAAELCCGL                      GRK4γ
AYAYETKDAL CLVLTIMNGG DLKFHIYNLG NPGFDEQRAV FYAAELCCGL                      GRK4δ
AYAYETKDAL CLVLTIMNGG DLKFHIYNLG NPGFDEQRAV FYAAELCCGL                      GRK4ε
AYAYETKDAL CLVLTIMNGG DLKFHIYNLG NPGFDEQRAV FYAAELCCGL                      GRK4ζ

EDLQRERIVY RDLKPENILL DDRGHIRISD LGLATEIPEG QRVRGRVGTV         350          GRK4α
EDLQRERIVY RDLKPENILL DDRGHIRISD LGLATEIPEG QRVRGRVGTV                      GRK4β
EDLQRERIVY RDLKPENILL DDRGHIRISD LGLATEIPEG QRVRGRVGTV                      GRK4γ
EDLQRERIVY RDLKPENILL DDRGHIRISD LGLATEIPEG QRVRGRVGTV                      GRK4δ
EDLQRERIVY RDLKPENILL DDRGHIRISD LGLATEIPEG QRVRGRVGTV                      GRK4ε
EDLQRERIVY RDLKPENILL DDRGHIRISD LGLATEIPEG QRVRGRVGTV                      GRK4ζ

GYMAPEVVNN EKYTFSPDWW GLGCLIYEMI QGHSPFKKYK EKVKWEEVDQ         400          GRK4α
GYMAPEVVNN EKYTFSPDWW GLGCLIYEMI QGHSPFKKYK EKVKWEEVDQ                      GRK4β
GYMAPEVVNN EKYTFSPDWW GLGCLIYEMI QGHSPFKKYK EKVKWEEVDQ                      GRK4γ
GYMAPEVVNN EKYTFSPDWW GLGCLIYEMI QGHSPFKKYK EKVKWEEVDQ                      GRK4δ
GYMAPEVVNN EKYTFSPDWW GLGCLIYEMI QGHSPFKKYK EKVKWEEVDQ                      GRK4ε
GYMAPEVVNN EKYTFSPDWW GLGCLIYEMI QGHSPFKKYK EKVKWEEVDQ                      GRK4ζ

RIKNDTEEYS EKFSEDAKSI CRMLLTKNPS KRLGCRGEGA AGVKQHPVFK         450          GRK4α
RIKNDTEEYS EKFSEDAKSI CRMLLTKNPS KRLGCRGEGA AGVKQHPVFK                      GRK4β
RIKNDTEEYS EKFSEDAKSI CRMLLTKNPS KRLGCRGEGA AGVKQHPVFK                      GRK4γ
RIKNDTEEYS EKFSEDAKSI CRMLLTKNPS KRLGCRGEGA AGVKQHPVFK                      GRK4δ
RIKNDTEEYS EKFSEDAKSI CRM------- ---------- ----------                     GRK4ε
RIKNDTEEYS EKFSEDAKSI CRM------- ---------- ----------                     GRK4ζ

DINFRRLEAN MLEPPFCPDP HAVYCKDVLD IEQFSAVKGI YLDTADEDFY         500          GRK4α
DINFRRLEAN MLEPPFCPDP HAVYCKDVLD IEQFSAVKGI YLDTADEDFY                      GRK4β
DINFRRLEAN MLEPPFCPDP HAVYCKDVLD IEQFSAVKGI YLDTADEDFY                      GRK4γ
DINFRRLEAN MLEPPFCPDP HAVYCKDVLD IEQFSAVKGI YLDTADEDFY                      GRK4δ
---------- --------P HAVYCKDVLD IEQFSAVKGI YLDTADEDFY                       GRK4ε
---------- --------P HAVYCKDVLD IEQFSAVKGI YLDTADEDFY                       GRK4ζ

ARFATGCVSI PWQNEMIESG CFKDINKSES EEALPLDLDK NIHTPVSRPN         550          GRK4α
ARFATGCVSI PWQNEMIESG CFKDINKSES EEALPLDLDK NIHTPVSRPN                      GRK4β
ARFATGCVSI PWQNE----- ---------- ---------- ----------                     GRK4γ
ARFATGCVSI PWQNE----- ---------- ---------- ----------                     GRK4δ
ARFATGCVSI PWQNE----- ---------- ---------- ----------                     GRK4ε
ARFATGCVSI PWQNE----- ---------- ---------- ----------                     GRK4ζ

RGFFYRLFRR GGCLTMVPSE KEVEPKQC                                 578          GRK4α
```

(SEQ ID NO: 1)

TABLE 1-continued

| | | |
|---|---|---|
| RGFFYRLFRR GGCLTMVPSE KEVEPKQC | 546 | GRK4β (SEQ ID NO: 2) |
| ---------- -GCLTMVPSE KEVEPKQC | 532 | GRK4γ (SEQ ID NO: 3) |
| ---------- -GCLTMVPSE KEVEPKQC | 500 | GRK4δ (SEQ ID NO: 4) |
| ---------- -GCLTMVPSE KEVEPKQC | 486 | GRK4ε (SEQ ID NO: 5) |
| ---------- -GCLTMVPSE KEVEPKQC | 454 | GRK4ζ (SEQ ID NO: 6) |

Note:
The bolded letters indicate the change in amino acid associated with hypertension R to L (argnine to leucine), A to V (alanine to valine), and A to V (alanine to valine).

Nucleotide sequence:

```
1
gcagccgccg cggtcgggct gccccctccc ctcgccccga ccgctcccct gctggtgagg    GRK4α
gcagccgccg cggtcgggct gccccctccc ctcgccccga ccgctcccct gctggtgagg    GRK4β
gcagccgccg cggtcgggct gccccctccc ctcgccccga ccgctcccct gctggtgagg    GRK4γ
gcagccgccg cggtcgggct gccccctccc ctcgccccga ccgctcccct gctggtgagg    GRK4δ

61
gcctgcgcag gcggcggcgg cggcgcccctt ggtggcagtg gtggcggcgg agcagcctcc    GRK4α
gcctgcgcag gcggcggcgg cggcgcccctt ggtggcagtg gtggcggcgg agcagcctcc    GRK4β
gcctgcgcag gcggcggcgg cggcgcccctt ggtggcagtg gtggcggcgg agcagcctcc    GRK4γ
gcctgcgcag gcggcggcgg cggcgcccctt ggtggcagtg gtggcggcgg agcagcctcc    GRK4δ

121
cgggatcgtg tctggagctc gaggagaggg tagtgcccgg cgagctatgc acgggggcgg    GRK4α
cgggatcgtg tctggagctc gaggagaggg tagtgcccgg cgagctatgc acgggggcgg    GRK4β
cgggatcgtg tctggagctc gaggagaggg tagtgcccgg cgagctatgc acgggggcgg    GRK4γ
cgggatcgtg tctggagctc gaggagaggg tagtgcccgg cgagctatgc acgggggcgg    GRK4δ

181
cggcgtctcc tcctgttccg cctcctcagt ctcctcggtc tcgcagaatc cgccggcggc    GRK4α
cggcgtctcc tcctgttccg cctcctcagt ctcctcggtc tcgcagaatc cgccggcggc    GRK4β
cggcgtctcc tcctgttccg cctcctcagt ctcctcggtc tcgcagaatc cgccggcggc    GRK4γ
cggcgtctcc tcctgttccg cctcctcagt ctcctcggtc tcgcagaatc cgccggcggc    GRK4δ
         exon 1

241
ggcggcgcca ggacatggag ctcgagaaca tcgtggccaa ctcgctgctg ctgaaagcgc    GRK4α
ggcggcgcca ggacatggag ctcgagaaca tcgtggccaa ctcgctgctg ctgaaagcgc    GRK4β
ggcggcgcca ggacatggag ctcgagaaca tcgtggccaa ctcgctgctg ctgaaagcgc    GRK4γ
ggcggcgcca ggacatggag ctcgagaaca tcgtggccaa ctcgctgctg ctgaaagcgc    GRK4δ
               atggag ctcgagaaca tcgtggccaa ctcgctgctg ctgaaagcgc    GRK4ε
               atggag ctcgagaaca tcgtggccaa ctcgctgctg ctgaaagcgc    GRK4ζ
         exon 2

301
gtcaaggagg atatggcaaa aaaagtggtc gtagtaaaaa atggaaggag atactgacac    GRK4α
gtcaa----- ---------- ---------- ---------- ---------- ----------    GRK4β
gtcaaggagg atatggcaaa aaaagtggtc gtagtaaaaa atggaaggag atactgacac    GRK4γ
gtcaa----- ---------- ---------- ---------- ---------- ----------    GRK4δ
gtcaaggagg atatggcaaa aaaagtggtc gtagtaaaaa atggaaggag atactgacac    GRK4ε
gtcaa----- ---------- ---------- ---------- ---------- ----------    GRK4ζ
         exon 3

361
tgcctcctgt cagccagtgc agtgagctta gacattccat tgaaaaggat tatagcagtc    GRK4α
---------- ---------- ---------- ---------- -gaaaaggat tatagcagtc    GRK4β
tgcctcctgt cagccagtgc agtgagctta gacattccat tgaaaaggat tatagcagtc    GRK4γ
---------- ---------- ---------- ---------- -gaaaaggat tatagcagtc    GRK4δ
tgcctcctgt cagccagtgc agtgagctta gacattccat tgaaaaggat tatagcagtc    GRK4ε
---------- ---------- ---------- ---------- -gaaaaggat tatagcagtc    GRK4ζ

421
tttgtgacaa gcaaccgata ggaagacgtc tcttcaggca gttctgtgat accaaaccca    GRK4α
tttgtgacaa gcaaccgata ggaagacgtc tcttcaggca gttctgtgat accaaaccca    GRK4β
```

TABLE 1-continued

```
     tttgtgacaa gcaaccgata ggaagacgtc tcttcaggca gttctgtgat accaaaccca     GRK4γ
     tttgtgacaa gcaaccgata ggaagacgtc tcttcaggca gttctgtgat accaaaccca     GRK4δ
     tttgtgacaa gcaaccgata ggaagacgtc tcttcaggca gttctgtgat accaaaccca     GRK4ε
     tttgtgacaa gcaaccgata ggaagacgtc tcttcaggca gttctgtgat accaaaccca     GRK4ζ
                                              exon 4

481
     ctctaaagag gcacattgaa ttcttggatg cagtggcaga atatgaagtt gccgatgatg     GRK4α
     ctctaaagag gcacattgaa ttcttggatg cagtggcaga atatgaagtt gccgatgatg     GRK4β
     ctctaaagag gcacattgaa ttcttggatg cagtggcaga atatgaagtt gccgatgatg     GRK4γ
     ctctaaagag gcacattgaa ttcttggatg cagtggcaga atatgaagtt gccgatgatg     GRK4δ
     ctctaaagag gcacattgaa ttcttggatg cagtggcaga atatgaagtt gccgatgatg     GRK4ε
     ctctaaagag gcacattgaa ttcttggatg cagtggcaga atatgaagtt gccgatgatg     GRK4ζ
                                              exon 5

541
     aggaccgaag tgattgtgga ctgtcaatct tagatagatt cttcaatgat aagttggcag     GRK4α
     aggaccgaag tgattgtgga ctgtcaatct tagatagatt cttcaatgat aagttggcag     GRK4β
     aggaccgaag tgattgtgga ctgtcaatct tagatagatt cttcaatgat aagttggcag     GRK4γ
     aggaccgaag tgattgtgga ctgtcaatct tagatagatt cttcaatgat aagttggcag     GRK4δ
     aggaccgaag tgattgtgga ctgtcaatct tagatagatt cttcaatgat aagttggcag     GRK4ε
     aggaccgaag tgattgtgga ctgtcaatct tagatagatt cttcaatgat aagttggcag     GRK4ζ

601
     ccccttttacc agaaatacct ccagatgttg tgacagaatg tagattggga ctgaaggagg     GRK4α
     ccccttttacc agaaatacct ccagatgttg tgacagaatg tagattggga ctgaaggagg     GRK4β
     ccccttttacc agaaatacct ccagatgttg tgacagaatg tagattggga ctgaaggagg     GRK4γ
     ccccttttacc agaaatacct ccagatgttg tgacagaatg tagattggga ctgaaggagg     GRK4δ
     ccccttttacc agaaatacct ccagatgttg tgacagaatg tagattggga ctgaaggagg     GRK4ε
     ccccttttacc agaaatacct ccagatgttg tgacagaatg tagattggga ctgaaggagg     GRK4ζ
                                              exon 6

661
     agaaccccttc caaaaaagcc tttgaggaat gtactagagt tgcccataac tacctaagag    GRK4α
     agaaccccttc caaaaaagcc tttgaggaat gtactagagt tgcccataac tacctaagag    GRK4β
     agaaccccttc caaaaaagcc tttgaggaat gtactagagt tgcccataac tacctaagag    GRK4γ
     agaaccccttc caaaaaagcc tttgaggaat gtactagagt tgcccataac tacctaagag    GRK4δ
     agaaccccttc caaaaaagcc tttgaggaat gtactagagt tgcccataac tacctaagag    GRK4ε
     agaaccccttc caaaaaagcc tttgaggaat gtactagagt tgcccataac tacctaagag    GRK4ζ

721
     gggaaccatt tgaagaatac caagaaagct catatttttc tcagttttta caatggaaat    GRK4α
     gggaaccatt tgaagaatac caagaaagct catatttttc tcagttttta caatggaaat    GRK4β
     gggaaccatt tgaagaatac caagaaagct catatttttc tcagttttta caatggaaat    GRK4γ
     gggaaccatt tgaagaatac caagaaagct catatttttc tcagttttta caatggaaat    GRK4δ
     gggaaccatt tgaagaatac caagaaagct catatttttc tcagttttta caatggaaat    GRK4ε
     gggaaccatt tgaagaatac caagaaagct catatttttc tcagttttta caatggaaat    GRK4ζ
                                              exon 7

781
     ggctggaaag gcaacccgta acaaagaaca catttagaca ttacagagtt ctaggaaaag    GRK4α
     ggctggaaag gcaacccgta acaaagaaca catttagaca ttacagagtt ctaggaaaag    GRK4β
     ggctggaaag gcaacccgta acaaagaaca catttagaca ttacagagtt ctaggaaaag    GRK4γ
     ggctggaaag gcaacccgta acaaagaaca catttagaca ttacagagtt ctaggaaaag    GRK4δ
     ggctggaaag gcaacccgta acaaagaaca catttagaca ttacagagtt ctaggaaaag    GRK4ε
     ggctggaaag gcaacccgta acaaagaaca catttagaca ttacagagtt ctaggaaaag    GRK4ζ
                                              exon 8

841
     gcggatttgg agaggtttgc gcctgtcaag tgcgagccac aggaaaaatg tatgcctgca    GRK4α
     gcggatttgg agaggtttgc gcctgtcaag tgcgagccac aggaaaaatg tatgcctgca    GRK4β
     gcggatttgg agaggtttgc gcctgtcaag tgcgagccac aggaaaaatg tatgcctgca    GRK4γ
     gcggatttgg agaggtttgc gcctgtcaag tgcgagccac aggaaaaatg tatgcctgca    GRK4δ
     gcggatttgg agaggtttgc gcctgtcaag tgcgagccac aggaaaaatg tatgcctgca    GRK4ε
     gcggatttgg agaggtttgc gcctgtcaag tgcgagccac aggaaaaatg tatgcctgca    GRK4ζ

901
     aaaagctaca aaaaaaaaga ataaagaaga ggaaaggtga agctatggct ctaaatgaga    GRK4α
     aaaagctaca aaaaaaaaga ataaagaaga ggaaaggtga agctatggct ctaaatgaga    GRK4β
     aaaagctaca aaaaaaaaga ataaagaaga ggaaaggtga agctatggct ctaaatgaga    GRK4γ
     aaaagctaca aaaaaaaaga ataaagaaga ggaaaggtga agctatggct ctaaatgaga    GRK4δ
     aaaagctaca aaaaaaaaga ataaagaaga ggaaaggtga agctatggct ctaaatgaga    GRK4ε
     aaaagctaca aaaaaaaaga ataaagaaga ggaaaggtga agctatggct ctaaatgaga    GRK4ζ
                                              exon 9

961
     aaagaattct ggagaaagtg caaagtagat tcgtagttag tttagcctac gcttatgaaa    GRK4α
     aaagaattct ggagaaagtg caaagtagat tcgtagttag tttagcctac gcttatgaaa    GRK4β
     aaagaattct ggagaaagtg caaagtagat tcgtagttag tttagcctac gcttatgaaa    GRK4γ
     aaagaattct ggagaaagtg caaagtagat tcgtagttag tttagcctac gcttatgaaa    GRK4δ
```

TABLE 1-continued

```
       aaagaattct ggagaaagtg caaagtagat tcgtagttag tttagcctac gcttatgaaa          GRK4ε
       aaagaattct ggagaaagtg caaagtagat tcatagttag tttagcctac gcttatgaaa          GRK4ζ

1021
       ccaaagatgc cttgtgcttg gtgctcacca ttatgaatgg aggggatttg aagtttcaca          GRK4α
       ccaaagatgc cttgtgcttg gtgctcacca ttatgaatgg aggggatttg aagtttcaca          GRK4β
       ccaaagatgc cttgtgcttg gtgctcacca ttatgaatgg aggggatttg aagtttcaca          GRK4γ
       ccaaagatgc cttgtgcttg gtgctcacca ttatgaatgg aggggatttg aagtttcaca          GRK4δ
       ccaaagatgc cttgtgcttg gtgctcacca ttatgaatgg aggggatttg aagtttcaca          GRK4ε
       ccaaagatgc cttgtgcttg gtgctcacca ttatgaatgg aggggatttg aagtttcaca          GRK4ζ

1081
       tttacaacct gggcaatccc ggctttgatg agcagagagc cgttttctat gctgcagagc          GRK4α
       tttacaacct gggcaatccc ggctttgatg agcagagagc cgttttctat gctgcagagc          GRK4β
       tttacaacct gggcaatccc ggctttgatg agcagagagc cgttttctat gctgcagagc          GRK4γ
       tttacaacct gggcaatccc ggctttgatg agcagagagc cgttttctat gctgcagagc          GRK4δ
       tttacaacct gggcaatccc ggctttgatg agcagagagc cgttttctat gctgcagagc          GRK4ε
       tttacaacct gggcaatccc ggctttgatg agcagagagc cgttttctat gctgcagagc          GRK4ζ
                                                                 exon 10

1141
       tgtgttgcgg cttggaagat ttacagaggg aaagaattgt atacagagac ttgaagcctg          GRK4α
       tgtgttgcgg cttggaagat ttacagaggg aaagaattgt atacagagac ttgaagcctg          GRK4β
       tgtgttgcgg cttggaagat ttacagaggg aaagaattgt atacagagac ttgaagcctg          GRK4γ
       tgtgttgcgg cttggaagat ttacagaggg aaagaattgt atacagagac ttgaagcctg          GRK4δ
       tgtgttgcgg cttggaagat ttacagaggg aaagaattgt atacagagac ttgaagcctg          GRK4ε
       tgtgttgcgg cttggaagat ttacagaggg aaagaattgt atacagagac ttgaagcctg          GRK4ζ
                                     exon 11

1201
       agaatattct ccttgatgat cgtggacaca tccggatttc agacctcggt ttggccacag          GRK4α
       agaatattct ccttgatgat cgtggacaca tccggatttc agacctcggt ttggccacag          GRK4β
       agaatattct ccttgatgat cgtggacaca tccggatttc agacctcggt ttggccacag          GRK4γ
       agaatattct ccttgatgat cgtggacaca tccggatttc agacctcggt ttggccacag          GRK4δ
       agaatattct ccttgatgat cgtggacaca tccggatttc agacctcggt ttggccacag          GRK4ε
       agaatattct ccttgatgat cgtggacaca tccggatttc agacctcggt ttggccacag          GRK4ζ
                                                                 exon 12

1261
       agatcccaga aggacagagg gttcgaggaa gagttggaac agtcggctac atggcacctg          GRK4α
       agatcccaga aggacagagg gttcgaggaa gagttggaac agtcggctac atggcacctg          GRK4β
       agatcccaga aggacagagg gttcgaggaa gagttggaac agtcggctac atggcacctg          GRK4γ
       agatcccaga aggacagagg gttcgaggaa gagttggaac agtcggctac atggcacctg          GRK4δ
       agatcccaga aggacagagg gttcgaggaa gagttggaac agtcggctac atggcacctg          GRK4ε
       agatcccaga aggacagagg gttcgaggaa gagttggaac agtcggctac atggcacctg          GRK4ζ

1321
       aagttgtcaa taatgaaaag tatacgttta gtcccgattg gtggggactt ggctgtctga          GRK4α
       aagttgtcaa taatgaaaag tatacgttta gtcccgattg gtggggactt ggctgtctga          GRK4β
       aagttgtcaa taatgaaaag tatacgttta gtcccgattg gtggggactt ggctgtctga          GRK4γ
       aagttgtcaa taatgaaaag tatacgttta gtcccgattg gtggggactt ggctgtctga          GRK4δ
       aagttgtcaa taatgaaaag tatacgttta gtcccgattg gtggggactt ggctgtctga          GRK4ε
       aagttgtcaa taatgaaaag tatacgttta gtcccgattg gtggggactt ggctgtctga          GRK4ζ

1381
       tctatgaaat gattcaggga cattctccat tcaaaaaata caaagagaaa gtcaaatggg          GRK4α
       tctatgaaat gattcaggga cattctccat tcaaaaaata caaagagaaa gtcaaatggg          GRK4β
       tctatgaaat gattcaggga cattctccat tcaaaaaata caaagagaaa gtcaaatggg          GRK4γ
       tctatgaaat gattcaggga cattctccat tcaaaaaata caaagagaaa gtcaaatggg          GRK4δ
       tctatgaaat gattcaggga cattctccat tcaaaaaata caaagagaaa gtcaaatggg          GRK4ε
       tctatgaaat gattcaggga cattctccat tcaaaaaata caaagagaaa gtcaaatggg          GRK4ζ

1441
       aggaggtcga tcaaagaatc aagaatgata ccgaggagta ttctgagaag ttttcagagg          GRK4α
       aggaggtcga tcaaagaatc aagaatgata ccgaggagta ttctgagaag ttttcagagg          GRK4β
       aggaggtcga tcaaagaatc aagaatgata ccgaggagta ttctgagaag ttttcagagg          GRK4γ
       aggaggtcga tcaaagaatc aagaatgata ccgaggagta ttctgagaag ttttcagagg          GRK4δ
       aggaggtcga tcaaagaatc aagaatgata ccgaggagta ttctgagaag ttttcagagg          GRK4ε
       aggaggtcga tcaaagaatc aagaatgata ccgaggagta ttctgagaag ttttcagagg          GRK4ζ
                                                   exon 13

1501
       atgccaaatc tatctgcagg atgttactca ccaagaatcc aagcaagcgg ctgggctgca          GRK4α
       atgccaaatc tatctgcagg atgttactca ccaagaatcc aagcaagcgg ctgggctgca          GRK4β
       atgccaaatc tatctgcagg atgttactca ccaagaatcc aagcaagcgg ctgggctgca          GRK4γ
       atgccaaatc tatctgcagg atgttactca ccaagaatcc aagcaagcgg ctgggctgca          GRK4δ
       atgccaaatc tatctgcagg atg------- ---------- ---------- ----------          GRK4ε
       atgccaaatc tatctgcagg atg------- ---------- ---------- ----------          GRK4ζ
```

TABLE 1-continued

```
1561
ggggcgaggg agcggctggg gtgaagcagc accccgtgtt caaggacatc aacttcagga    GRK4α
ggggcgaggg agcggctggg gtgaagcagc accccgtgtt caaggacatc aacttcagga    GRK4β
ggggcgaggg agcggctggg gtgaagcagc accccgtgtt caaggacatc aacttcagga    GRK4γ
ggggcgaggg agcggctggg gtgaagcagc accccgtgtt caaggacatc aacttcagga    GRK4δ
---------- ---------- ---------- ---------- ---------- ----------    GRK4ε
---------- ---------- ---------- ---------- ---------- ----------    GRK4ζ
                              exon 14

1621
ggctggaggc aaacatgctg gagcccctt tctgtcctga tcctcatgcc gtttactgta     GRK4α
ggctggaggc aaacatgctg gagcccctt tctgtcctga tcctcatgcc gtttactgta     GRK4β
ggctggaggc aaacatgctg gagcccctt tctgtcctga tcctcatgcc gtttactgta     GRK4γ
ggctggaggc aaacatgctg gagcccctt tctgtcctga tcctcatgcc gtttactgta     GRK4δ
---------- ---------- ---------- ---------- -cctcatgcc gtttactgta    GRK4ε
---------- ---------- ---------- ---------- -cctcatgcc gtttactgta    GRK4ζ

1681
aggacgtcct ggatatcgag cagttctcgg cggtgaaagg gatctacctg gacaccgcag    GRK4α
aggacgtcct ggatatcgag cagttctcgg cggtgaaagg gatctacctg gacaccgcag    GRK4β
aggacgtcct ggatatcgag cagttctcgg cggtgaaagg gatctacctg gacaccgcag    GRK4γ
aggacgtcct ggatatcgag cagttctcgg cggtgaaagg gatctacctg gacaccgcag    GRK4δ
---------- ---------- ---------- ---------- -cctcatgcc gtttactgta    GRK4ε
---------- ---------- ---------- ---------- -cctcatgcc gtttactgta    GRK4ζ
                              exon 15

1741
atgaagactt ctatgctcgg tttgctaccg ggtgtgtctc catcccctgg cagaatgaga    GRK4α
atgaagactt ctatgctcgg tttgctaccg ggtgtgtctc catcccctgg cagaatgaga-   GRK4β
atgaagactt ctatgctcgg tttgctaccg ggtgtgtctc catcccctgg cagaatgaga--  GRK4γ
atgaagactt ctatgctcgg tttgctaccg ggtgtgtctc catcccctgg cagaatga_-    GRK4δ
atgaagactt ctatgctcgg tttgctaccg ggtgtgtctc catcccctgg cagaatga--    GRK4ε
atgaagactt ctatgctcgg tttgctaccg ggtgtgtctc catcccctgg cagaatga--    GRK4ζ

1801
tgatcgaatc cgggtgtttc aaagacatca acaaaagtga aagtgaggaa gctttgccat    GRK4α
tgatcgaatc cgggtgtttc aaagacatca acaaaagtga aagtgaggaa gctttgccat    GRK4β
---------- ---------- ---------- ---------- ---------- ----------    GRK4γ
---------- ---------- ---------- ---------- ---------- ----------    GRK4δ
---------- ---------- ---------- ---------- ---------- ----------    GRK4ε
---------- ---------- ---------- ---------- ---------- ----------    GRK4ζ

1861
tagatctaga caagaacata catccccgg tttccagacc aaacagaggc ttcttctata    GRK4α
tagatctaga caagaacata catccccgg tttccagacc aaacagaggc ttcttctata    GRK4β
---------- ---------- ---------- ---------- ---------- ----------    GRK4γ
---------- ---------- ---------- ---------- ---------- ----------    GRK4δ
---------- ---------- ---------- ---------- ---------- ----------    GRK4ε
---------- ---------- ---------- ---------- ---------- ----------    GRK4ζ
                              exon 16

1921
gactcttcag aagaggggc tgcctgacca tggtccccag tgagaaggaa gtggaaccca     GRK4α
gactcttcag aagaggggc tgcctgacca tggtccccag tgagaaggaa gtggaaccca     GRK4β
---------- ------ggc tgcctgacca tggtccccag tgagaaggaa gtggaaccca     GRK4γ
---------- ------ggc tgcctgacca tggtccccag tgagaaggaa gtggaaccca     GRK4δ
---------- ------ggc tgcctgacca tggtccccag tgagaaggaa gtggaaccca     GRK4ε
---------- ------ggc tgcctgacca tggtccccag tgagaaggaa gtggaaccca     GRK4ζ

1981
agcaatgctg agcaccccgg tgcggaccac agagcagacc ctggcgccag gaaggagcat    GRK4α
agcaatgctg agcaccccgg tgcggaccac agagcagacc ctggcgccag gaaggagcat    GRK4β
agcaatgctg agcaccccgg tgcggaccac agagcagacc ctggcgccag gaaggagcat    GRK4γ
agcaatgctg agcaccccgg tgcggaccac agagcagacc ctggcgccag gaaggagcat    GRK4δ
agcaatgctg a                                                          GRK4ε
agcaatgctg a                                                          GRK4ζ

2041
gtgttagcgt ctcgtcccac ctggaattgt aataaataca tctaaataaa acatgccttg    GRK4α
gtgttagcgt ctcgtcccac ctggaattgt aataaataca tctaaataaa acatgccttg    GRK4β
gtgttagcgt ctcgtcccac ctggaattgt aataaataca tctaaataaa acatgccttg    GRK4γ
gtgttagcgt ctcgtcccac ctggaattgt aataaataca tctaaataaa acatgccttg    GRK4δ
                                                                     GRK4ε
                                                                     GRK4ζ

2101
ggagtgtaca gac    GRK4α (1857 bp, 16 exons)            (SEQ ID NO: 7)
ggagtgtaca gac    GRK4β (1761 bp, 15 exons, no exon 2) (SEQ ID NO: 8)
ggagtgtaca gac    GRK4γ (1719 bp, 15 exons, no exon 15)(SEQ ID NO: 9)
ggagtgtaca gac    GRK4δ (1623 bp, 14 exons, no exon 2 & 15) (SEQ ID NO: 10)
```

TABLE 1-continued

GRK4ε (1581 bp, 14 exons, no exon 13 & 15) (SEQ ID NO: 11)
GRK4ζ (1487 bp, 13 exons, no exon 2, 13, & 15) (SEQ ID NO: 12)

Note:
The bolded atg represents the start of translation.
The bolded and shaded nucleotides represent the
polymorphic sites associated with hypertension g
to t (exon 3), c to t (exon 5), and c to t (exon 14).
The exons are depicted by an underline and a double underline.
The nucleotides at 1989 to 1981 represent as stop codon.

A first aspect of Applicants' invention is directed to methods of screening individuals at risk for or who are susceptible or predisposed to essential hypertension. Essential hypertension is defined as hypertension of unknown etiology. Unlike some hypertensive diseases which have been fully characterized, there had been no known cause for essential hypertension. The identification of the association or relationship between the GRK4 gene, its basic functions and interaction with the D1 receptor, and essential hypertension allows for the screening of individuals to determine if they have a genetic basis for their measured high blood pressure or a predisposition to this disease if they present with a normal blood pressure. In the case of patients present with normal blood pressure (there are a variety of conditions that lead to false low blood pressure readings), but who also have clinical evidence for hypertension (such as end organ disease), the genetic screen for hypertensive mutations can be used to confirm the presence of hypertension. Thus, the individuals who are identified as predisposed to essential hypertension can then have their blood pressure more closely monitored and be treated, such as by way of diet modification, at an earlier time in the course of the disease.

One such diagnostic method entails isolating kidney cells having a D1 receptor and which express GRK4, from the individual. Kidney cells useful for conducting this method include renal proximal tubule cells and cortical collecting duct cells. They may be conveniently obtained from urine samples. The extent of the post-translational modification of the D1 receptor in the cells is then measured. A change in post-translational modification of the D1 receptor relative to cells isolated from a normotensive individual is believed to be caused by a change in GRK4 activity, and in turn is indicative of predisposition to essential hypertension. Several post-translational events may occur within such cells, including palmitoylation and phosphorylation. The D1 receptor in such cells isolated from a hypertensive individual exhibit what is known as hyperphosphorylation. By this term, it is meant that the amount of D1 receptors with attached phosphorus molecule is increased. Post-translational modifications can be detected and measured in accordance with standard techniques, such as immunoprecipitation of the D1 receptor with a D1 receptor antibody and immunoblotted against phosphoserine antibody, or labelling the cells with radioactive palmitic acid and immunoprecipitation with a D1 receptor antibody (Ng et al., Eur. J. Pharmacol. 267:7-19 (1994)).

Another such method entails obtaining a nucleic acid sample, e.g., DNA or RNA, from an individual and analyzing the nucleic acid sequence of the GRK4 gene of the individual for a mutation, whereby the presence of the mutation is indicative of predisposition of the individual to essential hypertension. The nucleic acid sample can be obtained from any cell type because GRK4 DNA is ubiquitous. The extraction of DNA from blood is a particularly suitable source. Referring to GRK4α numbering, preferred GRK4 mutants that are identified in this method include Arg→Leu at amino acid residue 65 (R65L), Ala→Val at amino acid residue 142 (A142V), Ala→Val at amino acid residue 486 (A486V), the double mutant R65L, A142V and R65L, A486V, and the triple mutant R65L, A142V, A486V. GRK4 alleles may be screened for mutations associated with essential hypertension directly or following cloning. Cloning can be connected using conventional techniques, e.g., by digesting genomic DNA into appropriate fragment sizes, and ligating the resulting fragments into a vector. On the other hand, polymerase chain reactions (PCRs) may be performed with primers for specific exons, e.g., exons 3, 5, 8, 14 and 16, of the GRK4 gene. Examples of such primers are set forth in Table 2. PCR can be formed on any sequence of the wild-type or mutant GRK4. PCR can also be performed on the GRK4 mRNA. Thus, those skilled in the art will appreciate that primers or primer pairs for the amplification of GRK4 alleles may be designed based on either nucleotide sequences identical in all isoforms and polymorphisms (as shown in Table 1), or they may be based on sequences that include the specific nucleotide substitution that results in the activating mutation. Other primers useful in practicing this aspect of the invention will amplify a DNA sequence including nucleotides 431-503 (exon 3), nucleotides 594-697 (exon 5), nucleotides 857-995 (exon 8), nucleotides 1662-1798 (exon 14), and nucleotides 1937-1991 (exon 16).

TABLE 2

Sequences of GRK4 primers (5' to 3')*.

| Exon | Direction | Sequence | | |
|------|-----------|----------|---|---|
| 3 | Forward | 33 - | AAAAGGATTATAGCAGTCTTTGTGACAA - 60 | (SEQ ID NO: 13) |
|   | Reverse | 118 - | CACTGCATCCAAGAATTCAATGTGCCTC - 143 | (SEQ ID NO: 14) |
| 5 | Forward | 35 - | CTAATGGTTATGTATTTGGTT - 55 | (SEQ ID NO: 15) |
|   | Reverse | 183 - | ATGCAGGGCTCAGCATGA - 200 | (SEQ ID NO: 16) |
| 8 | Forward | 92 - | AGGTGGACATAAACCTCC - 109 | (SEQ ID NO: 17) |
|   | Reverse | 292 - | CAAACAATGCACAGTGAAG - 309 | (SEQ ID NO: 18) |

TABLE 2-continued

Sequences of GRK4 primers (5' to 3')*.

| Exon | Direction | Sequence |
|---|---|---|
| 14 | Forward | 65 - CCTCATGCCGTTTACTGTAAGGACGTCC - 92 (SEQ ID NO: 19) |
|  | Reverse | 176- CTCATTCTGCCAGGGGATGGAGACACAC - 203 (SEQ ID NO: 20) |
| 16 | Forward | 90 - GCATCAGCCGTGTGCCT - 106 (SEQ ID NO: 21) |
|  | Reverse | 297 - GTGCAGAAGGTCTGTACA - 314 (SEQ ID NO: 22) |

*GenBank Accession #U33153 to U33168

The GRK4 alleles are tested for the presence of nucleic acid sequence different from the normal alleles by determining the nucleotide sequence of the cloned allele or amplified fragment and comparing it to the nucleotide sequence of the normal allele. Other known methods offer a more complete, yet somewhat indirect test for confirming the presence of an activating allele. These methods include single-stranded confirmation analysis, (SSCA), denaturing gradient gel electrophoresis (DGGE), RNase protection assays, allele-specific oligonucleotides (ASOs), the use of proteins which recognize nucleotide mismatches, such as the E. coli mutS protein, and allele-specific PCR. These methods are disclosed in Orita et al., Proc. Nat. Acad. Sci. USA 86:2766-2770 (1989); Sheffield et al., Proc. Nat. Acad. Sci. USA 86:232-236 (1989); Finkelstein et al., Genomics 7:167-172 (1990), and Kinszler et al., Science 251:1366-1370 (1991); Conner et al., Proc. Nat. Acad. Sci. USA 80:278-282 (1983); Modrich, Ann. Rev. Genet. 25:229-253 (1991); and Rano et al., Nucl. Acids Res. 17:8392 (1989), respectively. For allele-specific PCR, primers are used which hybridize at their 3' ends to a particular GRK4 mutation. If the GRK4 mutation is not present, an amplication product is not detected. Detection of amplification product may be conducted by Amplification Refractory Mutation System (ARMS), as disclosed in EP A 0332435.

In the first three methods (SSCA, DGGE and RNase protection assay), a new electrophoretic band appears. SSCA detects a band which migrates differentially because the sequence change causes a difference in single-strand intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type GRK4 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is seperated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the GRK4 mRNA or gene but can be a segment of either. If the riboprobe comprises only a segment of the GRK4 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA 85, 4397 (1988); Shenk et al., Proc. Natl. Acad. Sci. USA 72, 989 (1975); and Novack et al., Proc. Natl. Acad. Sci. USA 83, 586 (1986). Alternatively, mismatches can be detected by shifts in the electrophoretic mobility of mismatched duplexes relative to matched duplexes. See, e.g., Cariello, Human Genetics 42, 726 (1988). With either riboprobes or DNA probes, the cellular mRNA or DNA which might contain a mutation can be amplified using PCR before hybridization. Changes in DNA of the GRK4 gene can also be detected using Southern hybridization, especially if the changes are gross rearrangements, such as deletions and insertions.

DNA sequences of the GRK4 gene which have been amplified by use of PCR may also be screened using allele-specific probes. These probes are nucleic acid oligomers, each of which contains a region of the GRK4 gene sequence harboring a known mutation. For example, one oligomer may be about 30 nucleotides in length, corresponding to a portion of the GRK4 gene sequence. By use of a battery of such allele-specific probes, PCR amplification products can be screened to identify the presence of a previously identified mutation in the GRK4 gene. Hybridization of allele-specific probes with amplified GRK4 sequences can be performed, for example, on a nylon filter. Hybridization to a particular probe under stringent hybridization conditions indicates the presence of the same mutation in the DNA sample as in the allele-specific probe. Examples of such allele-specific probes are set forth in Table 3.

TABLE 3

Sequences of GRK4 allele specific oligonucleotides (5' to 3').

| Nucleotide Position* | Direction | Sequence |
|---|---|---|
| G448 | Reverse | CCTGAAGAGACGTCTTCCTA (SEQ ID NO: 23) |
| 448T | Reverse | CCTGAAGAGAAGTCTTCCTA (SEQ ID NO: 24) |
| C679 | Forward | CCAAAAAAGCCTTTGAGGA (SEQ ID NO: 25) |
| 679T | Forward | CCAAAAAAGTCTTTGAGGA (SEQ ID NO: 26) |
| G993 | Forward | AGTAGATTCGTAGTAAGTG (SEQ ID NO: 27) |
| 993A | Forward | AGTAGATTCATAGTAAGTG (SEQ ID NO: 28) |
| C1711 | Forward | AGTTCTCGGCGGTGAAAGG (SEQ ID NO: 29) |
| 1711T | Forward | AGTTCTCGGTGGTGAAAGG (SEQ ID NO: 30) |
| A1801 | Forward | TGTTGTAGGACTGCCTGA (SEQ ID NO: 31) |
| 1801G | Forward | TGTTGTAGGGCTGCCTGA (SEQ ID NO: 32) |

*based on GRK4, GenBank Accession # U33054

Mutations falling outside the coding region of GRK4 can be detected by examining the non-coding regions, such as introns and regulatory sequences near or within the GRK4 gene. An early indication that mutations in non-coding regions are important may come from Northern blot experiments that reveal messenger RNA molecules or abnormal size or abundance in hypertensive patients as compared to control individuals.

Alternation of GRK4 mRNA expression can be detected by any techniques known in the art. These include Northern blot analysis, PCR amplification and RNase protection. Diminished mRNA expression indicates an alteration of the wild-type GRK4 gene. Alteration of wild-type GRK4 genes can also be detected by screening for alteration of wild-type GRK4 gene. For example, monoclonal antibodies immunoreactive with GRK4 can be used to screen a tissue. Lack of cognate antigen would indicate a GRK4 gene mutation. Antibodies specific for products of mutant alleles could also be used to detect mutant GRK4 gene product. Such immunological assays can be done in any convenient formats known in the art. These include Western blots, immunohistochemical assays and ELISA assays. Any means for detecting an altered GRK4 can be used to detect alteration of wild-type GRK4 genes. Finding a mutant GRK4 gene product indicates alteration of a wild-type GRK4 gene.

Applicants speculate that GRK4 mutants other than the aforementioned six GRK4 mutants are associated with essential hypertension. Such mutants can be identified in vitro by measuring their ability to cause a D1 receptor-containing cell into which they are introduced not to transduce a dopaminergic signal. By this phrase, it is meant that the dopamine receptor fails to activate G protein subunits or fails to produce cytoplasmic second messengers that are needed to inhibit sodium transporters. Failure to transduce a dopaminergic signal is manifested in among other things, a D1 receptor/adenylyl cyclase (AC) or G protein coupling defect, and the post-translational modifications of the type described above. These phenomena can be measured by measuring the ability of, dopamine or its agonists to stimulate: (a) adenylyl cyclase activity or cAMP production or activate protein kinase A, (b) phospholipase C activity or activate protein kinase C, (c) phospholipase A2 activity, and (d) G-protein activity or inhibit sodium transport proteins such as the sodium/hydrogen exchanger or sodium/potassium ATPase.

Other GRK4s associated with essential hypertension can be identified by simply by sequencing a GRK4 gene obtained or cloned from an individual having essential hypertension.

Wild-type GRK4s or GRK4s associated with essential hypertension may be incorporated into a variety of systems in which to screen large numbers of different types of substances for anti-hypertensive activity. In general, any system that contains GRK4 and a GRK4 substrate, and from which GRK4 conformation or activity (and changes therein) can be measured, may be used in order to screen substances for anti-hypertensive activity. Thus, in the broadest sense of this aspect of the present invention, whole cells are not required. The system may be artificial in nature and housed within a lipid micelle, for example. See, Hammond et al., Nature 327: 730-732 (1987), for a discussion of cell-free systems in which to study molecular interactions. Whole cells are preferred, though, as is the D1 receptor, or a functional fragment thereof, as the GRK4 substrate. By the term "functional fragment, it is meant any part of the receptor, which is phosphorylated, palmitoylated or post-translationally modified by other means in vitro. A preferred method according to the present invention entails the use of cells transformed with a GRK4 nucleic acid. In general, a large variety of cell types can be used including mammalian, bacterial and insect cells. Mammalian cell lines such as Chinese hamster ovary (CHO) cells, human embryonic kidney (HEK) fibroblast (LTK) cells, MDCK and LLCPK cells are preferred. CHO cells are more preferred because they are expected to perform similarly to proximal tubule cells in vivo. Transforming cells with the GRK4 and D1 receptor nucleic acids may be conducted in accordance with standard procedures. See, e.g., Sambrook et al., *Molecular Cloning: A Laboratory Manual*, Cold Spring Harbor Laboratory, Cold Spring Harbor, N.Y. (1989), and Ausubel et al., *Current Protocols in MolecularBiology*, Wiley & Sons (1994).

In a more preferred embodiment of this aspect of Applicants' invention, the method is conducted using immortalized renal proximal tubule cells prepared using tubule cells isolated from a normotensive or hypertensive animal such as a human. In general, tubule cells are isolated from the kidney by cutting the cortex into small sections (e.g., 1 mm$^3$) and placing them on a suitable growth surface of a container (e.g., collagen-coated T-flasks.) After attachment is allowed by inverting the containers (e.g., for about 30 minutes at room temperature), the containers are righted and appropriate medium is added. Preferred medium is Dulbecco's Minimal Essential and F-12 medium with added substances (wt/ml): insulin (5 micrograms), transferrin (5 micrograms), selenium (5 nanograms), hydrocortisone (36 nanograms), triiodothyronine (4 picograms), and epidermal growth factor (19 nanograms). The tissues are incubated, left undisturbed for about three days at 37° C. in 95% air, 5% $CO_2$. See, Detrisac, et al., Kidney Int. 25:383-390 (1984). Alternatively, the pieces of cortex can be digested with collagenase, progressively sieved at 212 and 140 micrometers and concentrated over a 40-micrometer sieve prior to culturing. See, Courjault-Gautier et al., J. Am. Soc. Nephrol. 5:1949-1963 (1994). By the term "immortalized" it is meant that the cells grow indefinitely in culture. The isolated renal proximal tubule cells may be immortalized by infecting them with a retro-virus such as SV40 virus, et al., SV40tsA mutant virus and then obtaining outgrowing cells about 7-8 weeks after infection. These cells offer the advantage of more closely mimicking the in vivo environment in which the GRK4 protein functions. The immortalized cells from hypertensive subjects offer an almost limitless supply of cells that can be used to screen agents for anti-hypertensive activity.

Substances or agents possessing putative anti-hypertensive properties may be identified by determining a change in GRK4 confomation or activity upon addition of the substance or agent to the GRK4 system. GRK4 activity may be determined indirectly, such as by measuring adenylyl cyclase activity, or directly such as by measuring the extent of phosphorylation of a phosphorylatable substrate added to the culture. Any GRK4 activating or inactivating mutants, e.g., mutants or polymorphisms of GRK4 that lead to an increase in GRK4 activity or a decrease in GRK4 activity, respectively, are of interest. The alteration in GRK4 activity can lead to alteration in the function of G protein-coupled receptors exemplified by the D1 receptor. GRK4 may regulate the function of other proteins involved in essential hypertension such as the renin-angiotensin system, kallikrein-kinins, endothelins, atrial and brain natriuretic peptide, nitric oxide, serotonin, vasopressin, calcium sensing receptor, and epithelial sodium channel.

Another type of screening agent involves a complex between a GRK4 protein, e.g., wild-type or an isoform or mutant that is associated with essential hypertension, and an agent that causes a conformational change of the GRK4 protein upon interaction with an anti-hypertensive agent to be detected. The choice of the complexing agent depends upon the method in which conformational analysis is conducted. Such analysis may be conduced by spectrophometry, fluorescence, nuclear magnetic resonance, evanescent wave technology and atomic force microscopy.

Yet another type of screening agent and protocol involves the use of a transgenic animal model of essential hypertension, wherein the animal expresses a transgenic nucleic acid encoding a wild-type GRK4 or a mutant GRK4 of the present invention. The expression of the mutant GRK4 manifests a phenotype which is characterized by hypertension and a decreased ability of the animal to excrete an acute or chronic sodium load. The transgenic models can also be used to test for the effects of dietary manipulation such as high calcium, high potassium and high magnesium that have been shown to lower blood pressure, on GRK4 expression and activity. Clearly, any animal with an excretory system can be used as a model of essential hypertension. Rodents such as mice are preferred.

The transgenic animal can be created in accordance with techniques known in the art. Applicable techniques for preparing transgenic animals are well known in the art. Any method can be used which provides for stable, inheritable, expressible incorporation of the transgene within the nuclear DNA of an animal. These transgenic animals are constructed using standard methods known in the art as set forth, for example, in U.S. Pat. Nos. 4,873,191; 5,849,578; 5,731,489; 5,614,396; 5,487,992; 5,464,764; 5,387,742; 5,347,075; 5,298,422; 5,288,846; 5,221,778; 5,175,384; 5,175,383; 4,873,191; and 4,736,866, as well as Burke et al., Methods in Enzymology 194:251-270 (1991), Capecchi, Science 244: 1288-1292 (1989), Davies et al., Nucleic Acids Research 20(11):2693-2698 (1992), Dickinson et al., Human Molecular Genetics 2(8):1299-1302 (1993), Huxley et al., Genomics 9:742-750 (1991), Jakobovits et al. Nature 362:255-261 (1993), Lamb et al., Nature Genetics 5:22-29 (1993), Pearson et al., Proc. Natl. Scad. Sci. 90:10578-10582 (1993), Rothstein, Methods in Enzymology 194:281-301 (1991), Schedl et al., Nature 362:258-261 (1993), and Strauss et al., Science 259:1904-1907 (1993). Further, published international patent applications WO 94/23049, WO 93/14200, WO 94/06908 and WO 94/28123 provide further relevant teachings in these regards.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., Proc. Natl. Acad. Sci., USA 82:6148-6152 (1985)); gene targeting in embryonic stem cells (Thompson et al., Cell 56:313-321 (1989)); electroporation of embryos (Lo, Mol. Cell. Biol. 3:1803-1814 (1983)); and sperm-mediated gene transfer (Lavitrano et al., 1989, Cell 57:717-723 (1989)). See Gordon, Transgenic Animals, Intl. Rev. Cytol. 115:171-229 (1989), for a general review on these techniques.

The present invention provides for transgenic animals that carry the GRK4 transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teachings of Lasko et al., Proc. Natl. Acad. Sci. USA 89:6232-6216 (1992). Those skilled in the art will appreciate that the regulatory sequences required for such a cell-type specific activation will depend upon the particular cell type of interest. When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene may also be selectively introduced into a particular cell type, thus inactivating the endogenous gene of interest in only that cell type, by following, for example, the teaching of Gu et al., Science 265:103-106 (1994). The regulatory sequences required for such a cell-type specific inactivation will depend upon the particular cell type of interest, and will be apparent to those of skill in the art.

Once transgenic animals have been generated, the expression of the recombinant target gene and protein may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene gene product of interest.

The target gene transgenic animals that express target gene mRNA or target gene transgene peptide (detected immunocytochemically, using antibodies directed against the target gene product's epitopes) at easily detectable levels should then be further evaluated to identify those animals which display characteristic symptoms of essential hypertension.

In a preferred embodiment, the GRK4 transgene is inserted into an appropriate vector, inoperable association with a tetracycline sensitive promoter, and then introduced into embryonic stem (ES) cells. The ES cells are then reintroduced by microinjection of the genetically altered ES cells into host blastocysts or by morulae co-culture. Founder animals are obtained and animals homozygous for the GRK4 transgene are then used. See, Thompson, et al., Am. J. Physiol. 269: E793-E803 (1995).

Therapeutic modalities entail targeting GRK4 activity to increase natriuresis or otherwise approach normalcy with respect to a proper balance of sodium and water. For example, GRK4 expression can be prevented by targeting at the RNA level or the DNA level by administering a drug that changes expression of GRK4 in kidney cells. Such drugs are preferably oligonucleotide molecules such as antisense oligonucleotides, dominant negative mutant DNA molecules, and ribozymes that reduce or prevent GRK4 expression by binding GRK4 mRNA, pre-mRNA, or GRK4 DNA. The administration of antisense oligonucleotides to a hypertensive individual can be conducted in accordance with the formulations and vehicles described in U.S. Pat. Nos. 5,856,099; 5,856,103; 5,783,683; 5,840,708; and 5,591,600; 5,849,903; 5,135,917; 5,098,890; and 5,087,617. Antisense technology, now well known in the art, is also described in Uhlmann et al., Chem. Rev. 90:543-584 (1990); Oligodeoxynucleotides: Antisense Inhibitors of Gene Expression (Cohen, ed. 1989); Delivery Strategies for Antisense Oligonucleotide Therapeutics, CRC press (Saghir Akhtar, ed. 1995); and Stein, C. A., and Cohen, Jack S., "Oligodeoxynucleotides as Inhibitors of Gene Expression: A Review," Cancer Research 48:2659-2668 (1988).

Synthetic antisense oligonucleotides should be of sufficient length to hybridize to the target nucleotide sequence and exert the desired effect, e.g., blocking translation of an mRNA molecule. It is advantageous, however, to use relatively smaller oligonucleotides because they are likely to be more efficiently taken up by cells in vivo, such that a greater number of antisense oligonucleotides are delivered to the location of the target mRNA. Preferably, antisense oligonucleotides should be at least 15 nucleotides long, and preferably 20 nucleotides in length, to achieve adequate specificity. Preferred antisense oligonucleotides are (5' CAC GAT GTT CTC GAG CTC CAT 3', (SEQ ID NO:33) complementary to bases 255-275 and 5' CTC CAT GTC CTG GCG CCG 3' (SEQ ID NO:34) complementary to bases 243-260.

Small oligonucleotides such as those described above are highly susceptible to degradation by assorted nucleases. Moreover, such molecules are may be unable to enter cells because of insufficient membrane permeability. For these reasons, practitioners skilled in the art generally synthesize oligonucleotides that are modified in various ways to increase stability and membrane permeability. The use of modified antisense oligonucleotides is preferred in the present invention. The term "antisense oligonucleotide analog" refers to such modified oligonucleotides, as discussed hereinbelow.

The oligonucleotides of the invention are conveniently synthesized using solid phase synthesis of known methodology, and are designed to be complementary to and/or specifically hybridizable with the preselected sequence of the target GRK4 DNA or RNA encoding the sequences disclosed herein. Nucleic acid synthesizers are commercially available and their use is understood by persons of ordinary skill in the art as being effective in generating any desired oligonucleotide of reasonable length.

Ribozymes, e.g., of the hammerhead or haripin types, that catalyze the degradation of GRK4 mRNA or pre-mRNA can be designed and prepared in accordance with standard procedures. See, e.g., U.S. Pat. No. 5,856,463 (and publications cited therein), for detailed teachings on methods of designing, making and formulating ribozymes for therapeutic uses.

GRK4 activity can also be targeted by administering agents such as pharmacologic antagonists or blockers that change (e.g., inhibit or enhance) catalytic activity, e.g., phosphorylating or non-phosphorylating action, of the fully or partially expressed GRK4 protein by acting directly upon the protein. Other therapeutic action entails direct binding of GRK4 protein with peptidic agents. All of these methods and agents result in a normalization of D1 receptor/AC coupling in kidney cells that express GRK4, and as a result, decreased sodium transport in renal proximal tubule cells.

The invention will be further described by reference to the following detailed examples. These examples are provided for purposes of illustration only, and are not intended to be limiting as to the scope of the invention described herein, unless otherwise specified.

EXAMPLES

Tissue Culture

Human kidneys were obtained as fresh surgical specimens from patients who had unilateral nephrectomy due to renal carcinoma. The patient records of the subjects were reviewed and classified into those with either normal blood pressure (n=9) or essential hypertension (n=14). Subjects with systolic blood pressures less than 140 mm Hg and diastolic blood pressures less than 90 mm Hg were considered normotensive. Subjects with systolic blood pressures equal to or greater than 140 mm Hg or diastolic blood pressures equal to or greater than 90 mm Hg and/or on antihypertensive medications were considered hypertensive.

Cultures of renal proximal tubule cells from histologically-verified normal kidney sections ($5 \times 10^5$ cells/well in 24 well plastic plates coated with 0.075% Type I collagen) were incubated at 37° C. in 95% $O_2$/5% $CO_2$ and grown in a serum-free medium consisting of a 1:1 mixture of Dulbecco's Modified Eagle's medium and Ham's F12 medium supplemented with selenium (5 ng/ml), insulin (5 μg/ml), transferrin (5 μg/ml), hydrocortisone (36 ng/ml), triiodothyronine (4 pg/ml), and epidermal growth factor (10 ng/ml). When sub-confluent (90-95%), the cells were sub-cultured (passages 6-8) for use in experimental protocols using trypsin-EDTA (0.05%, 0.02%). The culture conditions are conducive for growth of human renal proximal tubules that retain characteristics of renal proximal tubule cells, Sanada, et al., J. Invest. Med. 45:277 A (1997).

Light Microscopic Immunohistochemistry

Immunohistochemistry of kidney tissues and cells in culture fixed in HISTOCHOICE was performed as described Sanada, et al., supra. Affinity-column purified polyclonal human $D_1$ receptor antibodies were raised against a synthetic peptide sequence GSGETQPFC (amino acids 299-307). See, Sanada, et al., supra. Two commercially available GRK4 isoform antibodies were used (Santa Cruz Biotechnology, Inc, Santa Cruz, Calif.); one GRK4 antibody recognized both the α and β isoform, while another recognized both the αβ isoform. The specificity of these antibodies has been previously reported. Sanada, et al., supra, and Guyton A. C., *Circulatory Physiology III, Arterial Pressure and Hypertension*, W.B. Saunders Co., Philadelphia, Pa. (1980).

Immunohistochemistry studies have shown GRK4α/β and GRK4α/δ isoform expression only in renal proximal and distal convoluted tubules (not in loops of Henle, cortical or medullary collecting ducts, glomeruli or renal arterial vessels). GRK4α/ε was found in both luminal and basolateral membranes while GRKα/β was found in the luminal membrane only. There were no differences in the renal expression of these two GRK4 isoforms between hypertensive and normotensive subjects (not shown). The expression of GRK4α/β and GRK4α/δ persisted in renal proximal tubule cells in culture (photographs not shown).

Determination of GRK Activity

GRK activity was measured according to Benovic, Methods Enzymol. 200:351-362 (1991). Renal proximal tubular extracts were prepared by homogenization in ice-cold lysis buffer containing (in mM): 25 Tris-HCl, pH 7.5, 5 EDTA, and 5 EGTA with leupeptin (10 μg/ml), aprotinin (20 μg/ml), and 1 PMSF. The crude homogenate was centrifuged at 30,000 g for 30 min. The pellet was extracted by 200 mM NaCl on ice for 30 min and centrifuged at 30,000 g for 30 min. The supernatant was used for all GRK assays and immunoblotting. Twenty μg of protein extract was incubated with rhodopsin-enriched rod outer segments in assay buffer with 10 mM $MgCl_2$ and 0.1 mM ATP (containing $\gamma^{32}P$-ATP). After incubation in white light for 15 min at room temperature, the reaction was stopped with ice-cold lysis buffer and centrifuged at 13,000 g for 15 min. The pellet was resuspended in Laemmli buffer and subjected to 12% SDS-PAGE. The gels were subjected to autoradiography, and the phosphorylated rhodopsin was quantified using both densitometry and radioactive counting of the excised bands at the appropriate size. GRK activity was also measured in the presence or absence of a GRK isoform antibody.

FIG. 1 shows that the $D_1$-like agonist, fenoldopam, had no effect on GRK activity, assessed by the phosphorylation of rhodopsin, in renal proximal tubule cells from normotensive subjects. These data suggest that GRKs that can use rhodopsin as a substrate (i.e., GRK2, GRK3, GRK4α, GRK5, GRK6) are not involved in the desensitization of the $D_1$ receptor in renal proximal tubule cells when blood pressure is normal. It was also found that $D_1$ receptor and GRK4 expression in renal proximal tubule cells in culture were similar in hypertensive and normotensive subjects (data not shown). In renal proximal tubule cells from hypertensive subjects, however, fenoldopam increased GRK activity. Moreover, basal GRK activity in renal proximal tubule cells was greater in hypertensive than in normotensive subjects. These studies suggest an aberrant function of GRK in renal proximal tubules in hypertension.

The increase in GRK activity produced by fenoldopam (in hypertension) was blocked by antibodies to GRK2, GRK3, and GRK4α/δ (data not shown), indicating that activation of one or all of these GRKs may be involved in the fenoldopam-mediated increase in GRK activity. Tiberi et al., J. Biol. Chem. 271:3771-3778 (1996). However, the ubiquitous expression of GRK2 and GRK3 is at odds with the recognized pre-eminence of the kidney in the pathogenesis of both rodent and human essential hypertension. Guyton, W.B. Saunders Co. Phil., Pa. (1980); Guidi et al., J. Am. Soc. Nephrol. 7:1131-1138 (1996). No difference was found in the sequence of the coding region of GRK2 between hypertensive and normotensive human subjects (data not shown). This finding suggests that the increase in GRK2 activity in lymphocytes of hypertensive patients (Gros et al., J. Clin. Invest. 99:2087-2093 (1997)) is secondary to the high blood pressure, as has been suggested for the increase in GRK5 activity and expression in rodents with genetic and induced hypertension. Ishizaka et al., J. Biol. Chem. 272:32482-32488 (1997).

Determination of cAMP Accumulation

The cells were washed twice with Dulbecco's phosphate buffered saline (D-PBS), after which 1 mM 3-isobutyl-1-methyl-xanthine was added to each well. The cells were incubated at 37° C. for 30 minutes with or without drugs: dopamine and the $D_1$-like receptor agonist, fenoldopam, the $D_1$-like receptor antagonist, SCH23390 (Research Biochemicals International, Natick, Mass.), and forskolin (Sigma Chemical Co., St. Louis, Mo.). Then, the cells were washed twice with D-PBS and frozen at −80° C. and the cells were further lysed with 0.1N HCl. cAMP concentration was measured by radio-immunoassay. Sanada, et al., supra., and Kinoshita, S. J. Clin. Invest. 84:1849-1856 (1989). Protein concentration was measured with the BCA protein assay kit (Pierce Chem. Co., Rockford, Ill.).

Figure 2:
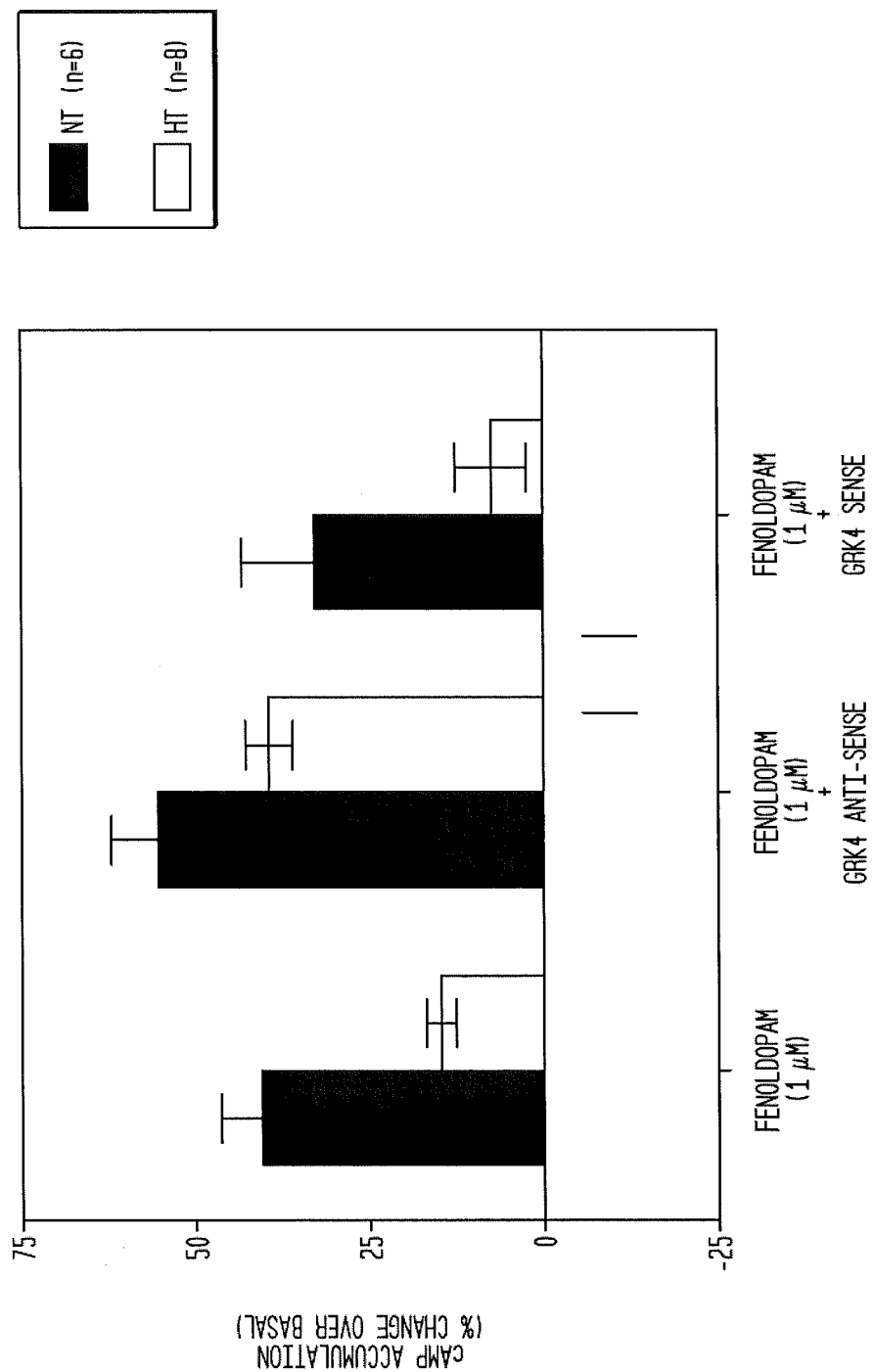
FIG. 2 is a graph that show that prevention of the expression of GRK4 restores to normal values the ability of renal proximal tubule cells from hypertensive subjects to increase cAMP production caused by a D1-like agonist.

To determine whether an increase in GRK4 activity was responsible for the uncoupling of the $D_1$ receptor in renal proximal tubule cells in hypertension, the effect of $D_1$-like agonist stimulation on cAMP accumulation after inhibition of the translation of GRK4 by antisense oligonucleotides was studied. FIG. 2 shows that the $D_1$-like agonist, fenoldopam, increased cAMP accumulation to a greater extent in renal proximal tubule cells from normotensive than from hypertensive subjects. Neither sense/scrambled nor antisense GRK4 oligonucleotides affected basal or forskolin-stimulated cAMP production. Compared with fenoldopam alone, neither sense nor scrambled GRK4 oligonucleotides significantly affected cAMP accumulation in either group. However, antisense GRK4 oligonucleotides enhanced the ability of fenoldopam to stimulate cAMP accumulation in cells from hypertensive subjects (but not from normotensive subjects) such that the values approximated those observed in cells from normotensive subjects treated with fenoldopam.

Immunoprecipitation

Proximal tubule cells were incubated with vehicle, fenoldopam, sense, scrambled or antisense propyne/phosphorothioate oligonucleotides (5 nM) as described above. The membranes were lyzed with ice cold lysis buffer (PBS with 1% NP40, 0.5% sodium deoxycholate, 0.1% SDS, 1 mM EDTA, 1 mM EGTA, 1 mM sodium vanadate, 1 mM NaF, 1 mM PMSF, 10 μg/ml aprotinin and 10 μg/ml leupeptin). The lysates were incubated with IgG-purified anti $D_1$ receptor antibody on ice for 1 hr and protein-A agarose for 12 hrs with rocking at 4° C. The proteins separated by SDS-polyacrylamide gel electrophoresis were electrophoretically transferred onto nitrocellulose membranes. The transblot sheets blocked with 5-10% nonfat dry milk in 10 mM Tris-HCl, pH 7.5, 150 mM NaCl, and 0.1% Tween-20 were incubated with diluted affinity-purified polyclonal anti-phosphoserine antibody (Zymed Lab, San Francisco, Calif.); Sanada, et al., supra. In some cases, the cells were labeled with $^{32}$P and immunoprecipitated with anti $D_1$ receptor antibody. The autoradiograms and immunoblots, visualized with ECL system (Amersham, Arlington Heights, Il) were quantified by densitometry. Sanada, et al., supra.

Figure 3:
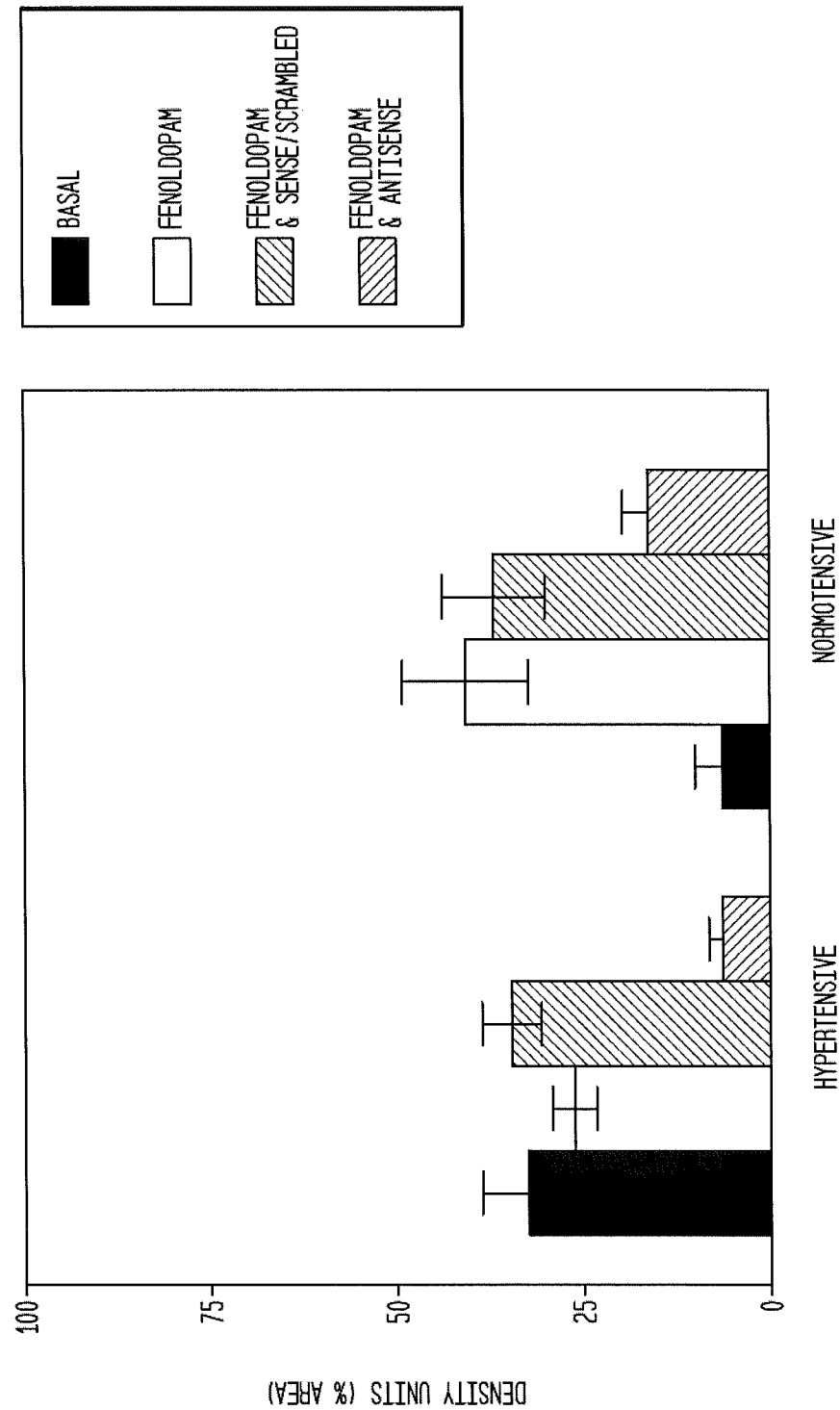
FIG. 3 is a graph that shows that the phosphorylation of D1 receptor in the resting proximal tubule cell which is greater in hypertensive subjects than in normotensive subjects does not respond to D1-like agonist stimulation. The phosphorylation of the D1 receptor can be abrogated if GRK4 expression is prevented.

The next study was directed to whether the differential effects of antisense GRK4 oligonucleotides extended to the phosphorylation of the $D_1$ receptor. FIG. 3 shows that the basal levels of serine-phosphorylated $D_1$ receptor in renal proximal tubule cells were greater in hypertensive than in normotensive subjects and correlated with the increased basal levels of GRK activity in hypertensive subjects (as shown in FIG. 1). Fenoldopam increased the quantity of serine-phosphorylated $D_1$ receptor in normotensive but not in hypertensive subjects in agreement with our previous report. Sanada, et al., supra. Neither sense nor scrambled GRK4 oligonucleotides affected the phosphorylation of the $D_1$ receptor in fenoldopam-treated cells in either group of subjects. In contrast, GRK4 antisense treatment almost completely abolished the phosphorylation of the $D_1$ receptor in fenoldopam-treated renal proximal tubule cells from hypertensive subjects to levels that are lower than basal values. GRK4 antisense treatment also decreased the phosphorylation of the $D_1$ receptor in fenoldopam-treated renal proximal tubule cells from normotensive subjects but the values remained above baseline levels. The almost complete suppression of the phosphorylation of the $D_1$ receptor by antisense oligonucleotides to GRK4 in renal proximal tubules in hypertensive subjects suggests that the major GRK involved in the phosphorylation and desensitization of the $D_1$ receptor in hypertension is GRK4 and not other GRKs that may be expressed in this nephron segment.

Genotyping

Based upon the initial observations that the incidence of homozygous GRK4 gene variants is about 60% in hypertensive subjects and 16% in the general population, power analysis (power of 0.8, a of 0.05, and effect of 45%) indicated a sample size of 14-21 per group to detect any significant differences between groups. For this reason, DNA from peripheral blood of additional 18 hypertensive and 11 normotensive subjects were obtained. All volunteers were examined and their medical records were reviewed by at least two investigators. Subjects were classified as normotensive if they had no history of hypertension, no clinical evidence of underlying hypertension, were taking no antihypertensive medications, were not receiving vasodilator therapy or other drugs that could affect blood pressure, and had sitting systolic blood pressures less than 140 mm Hg and diastolic blood pressures less than 90 mm Hg on their three most recent clinic visits. Patients with hypertension had significant and sustained elevations in blood pressures (greater than 160 mm Hg systolic and 95 mm Hg diastolic) on at least three separate occasions. All hypertensive subjects (DNA from kidney, n=14, DNA from peripheral blood, n=18) were at least 20 years old. To obviate the problem inherent in the late onset of essential hypertension in some individuals, all normotensive subjects (DNA from kidney, n=9, DNA from peripheral blood, n=11) were at least 45 years old.

Genomic DNA was extracted (salting out method) from renal proximal tubule cells in culture and kidney tissues or peripheral blood leukocytes of random. Exons of GRK4 containing polymorphic nucleotides were amplified with primers listed in Table 2. Each 20 µl reaction mixture contained 1×PCR buffer, 0.2 mM each dNTP, 1.25 mM $MgCl_2$, 0.2 µM each primer, 0.5 unit Taq DNA polymerase and 50 ng genomic DNA. The reaction mixture was denatured at 94° C.

for 5 min, followed by 30 cycles of 30 sec of denaturation at 94° C., 30 sec of reannealment at 55° C., and 30 sec of extension at 72° C. The PCR was completed by a final extension at 72° for 5 min. Two µl of PCR product were spotted onto a Biodyne B+ membrane. Dot blots were prepared for each of the following wild type and variant allele specific oligonucleotide probes (Table 4). Probe labeling, membrane preparation, hybridization, and washing conditions were those of published procedures. See Wong et al., Clin. Chem. 43:1857-1861 (1997). The nucleotide at position 1801 in 250 random subjects was invariant (G). It was also found that the frequency of the polymorphic nucleotide at position 993 was not different between hypertensive and normotensive subjects. Therefore, only the results of the studies of 3 polymorphic sites at positions 448, 679, and 1711 (Table 4) are presented. The sequences of the cDNA were determined by the Sanger dideoxy chain termination method.

TABLE 4

GRK4 variants in normotensive and hypertensive subjects.

| | Genotype | | |
|---|---|---|---|
| Phenotype | Homozygous R65L | Homozygous A142V | Homozygous A486V |
| Hypertensive (n = 32) | 6 | 11 | 4 |
| Normotensive (n = 20) | 1 | 0 | 0 |

Genotype was determined by dot blot analysis using allele specific oligonucleotides. Four hypertensive subjects were homozygous at two sites (amino acid position 65 and 142). The frequency of homozygous variants at R65L, A142V, and/or A486V in hypertensive subjects (53%, 17 of 32) was significantly different from that noted in normotensive subjects (5%, 1 of 20) ($\chi^2$=10.56, P=0.0012). The frequency of homozygous variant A142V was also significantly different ($\chi^2$=6.78, P=0.0092) between hypertensive (34%, 11 of 32) and normotensive subjects (0%, 0 of 20).

Sequencing of GRK4 cDNA from human kidneys and subsequent genotyping of 5 polymorphic sites in DNA from the kidney and peripheral white blood cells revealed that 3 variants: nucleotide 448, CGT to CTT (amino acid R65L), nucleotide 679, GCC to GTC (amino acid A142V), and nucleotide 1711, GCG to GTG (amino acid A486V) (autoradiograph not shown) occurred more frequently in hypertensive than in normotensive subjects (Table 4). The frequency of homozygous variations at R65L, A142V, and/or A486V in hypertensive subjects (53%, 17 of 32) was significantly different from that noted in χnormotensive subjects (5%, 1 of 20) ($\chi^2$=10.56, P=0.0012) (Table 4) and different from those found in a random population of 50 adult subjects ($\chi^2$=10.99, P=0.0009). In this random population with unknown blood pressure, 16% were homozygous at R65L and/or A486V and 50% were heterozygous at either R65L or A486V; the 16% frequency of homozygous alleles is close to the incidence of essential hypertension (Lifton, Science 272:676-680 (1996)). The homozygous variation at GRK4 A142V, by itself, was also more frequent in hypertensive (34%, of 32) than in normotensive subjects (0%, 0 of 20), ($\chi^2$=6.78, P=0.0092).

GRK4α is the only GRK4 isoform that has been reported to phosphorylate rhodopsin (Sallese et al., J. Biol. Chem. 272: 10188-10195 (1997)), but in our studies, $D_1$ agonist stimulation with fenoldopam failed to increase GRK activity in renal proximal tubule cells from normotensive subjects (FIG. 1).

Figure 4:
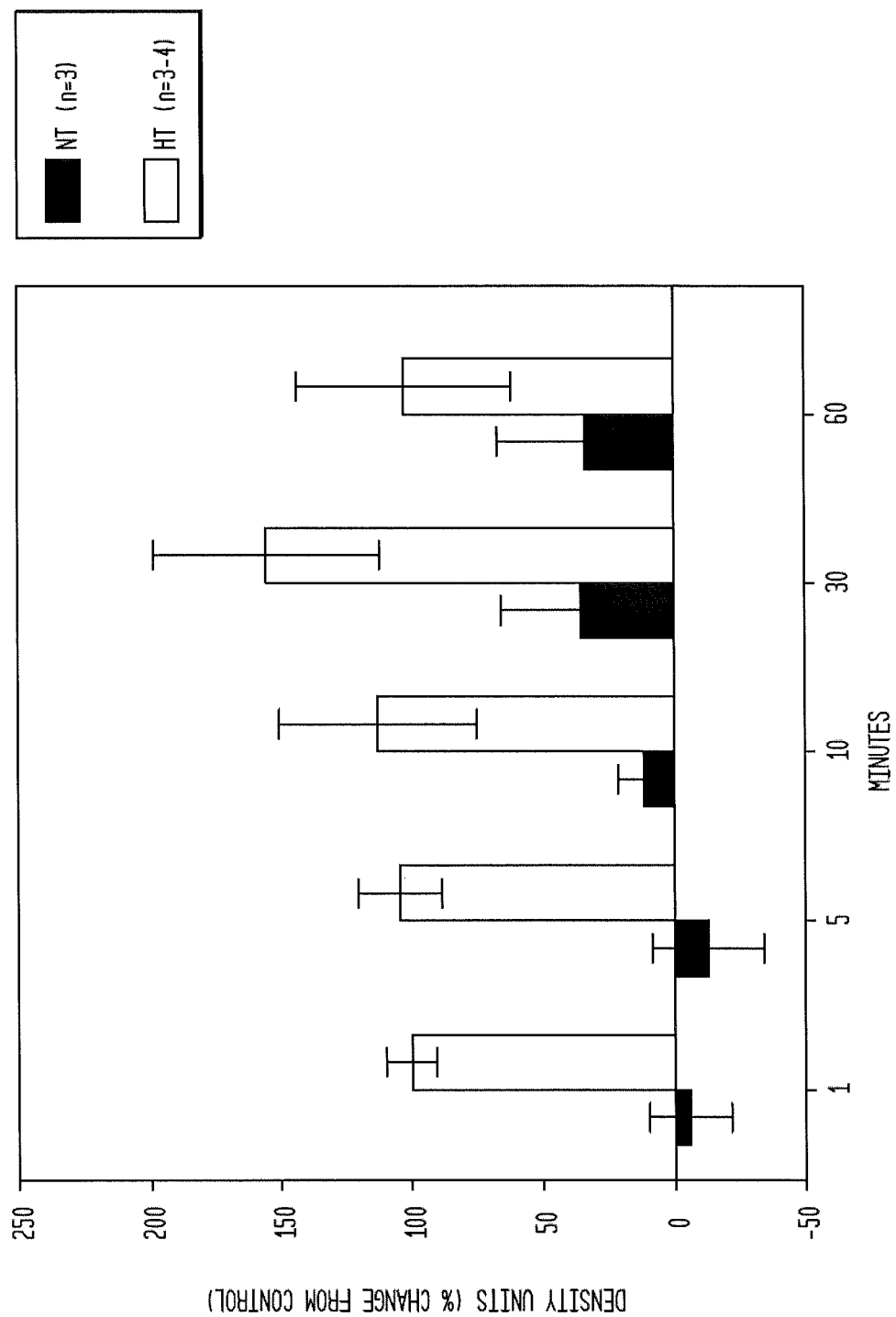
FIG. 4 is a graph that shows an increase in GRK4γ/δ expression in renal proximal tubules in response to D1-like agonist stimulation in hypertensive but not in normotensive subjects.

Therefore, it was concluded that GRK4α is not involved in the desensitization of the $D_1$ receptor. The belief is that a GRK4 isoform that does not normally phosphorylate rhodopsin (e.g., GRK4γ) (Premont et al., J. Biol. Chem. 271:6403-6410 (1996); Sallese et al., supra.; and Virlon et al., Endocrinol. 139:2784-2795 (1998)) may have become activated in hypertension. Indeed, it was found that the $D_1$-like agonist-mediated increase in GRK activity was associated with an increase in membranous expression of GRK4γ/δ in renal proximal tubule cells from hypertensive but not from normotensive subjects (FIG. 4).

Transfection and Cell Culture

The rat $D_1$ (r$D_1$) or human $D_1$ (h$D_1$) receptor cDNA was subcloned in the expression vector pPUR (Clontech, Palo Alto, Calif.) or pcDNA3.1/Zeo (Invitrogen, Carlsbad, Calif.), respectively, between EcoRI and XbaI sites. The resulting constructs were used to stably transfect CHO cells expressing the pTet-Off regulator plasmid (Clontech, Palo Alto, Calif.) using calcium phosphate. See Yamaguchi et al., Mol. Pharmacol. 49:373-378 (1996). GRK4γ and GRK4δcDNAs, obtained from RT/PCR of mRNA from human kidney cortex were subcloned into a pTet-Off response plasmid (pTRE-r$D_1$ or pTRE-h$D_1$ and pTK-Hyg mixed in a 20:1 ratio, respectively) (Clontech, Palo Alto, Calif.).

Figure 5:
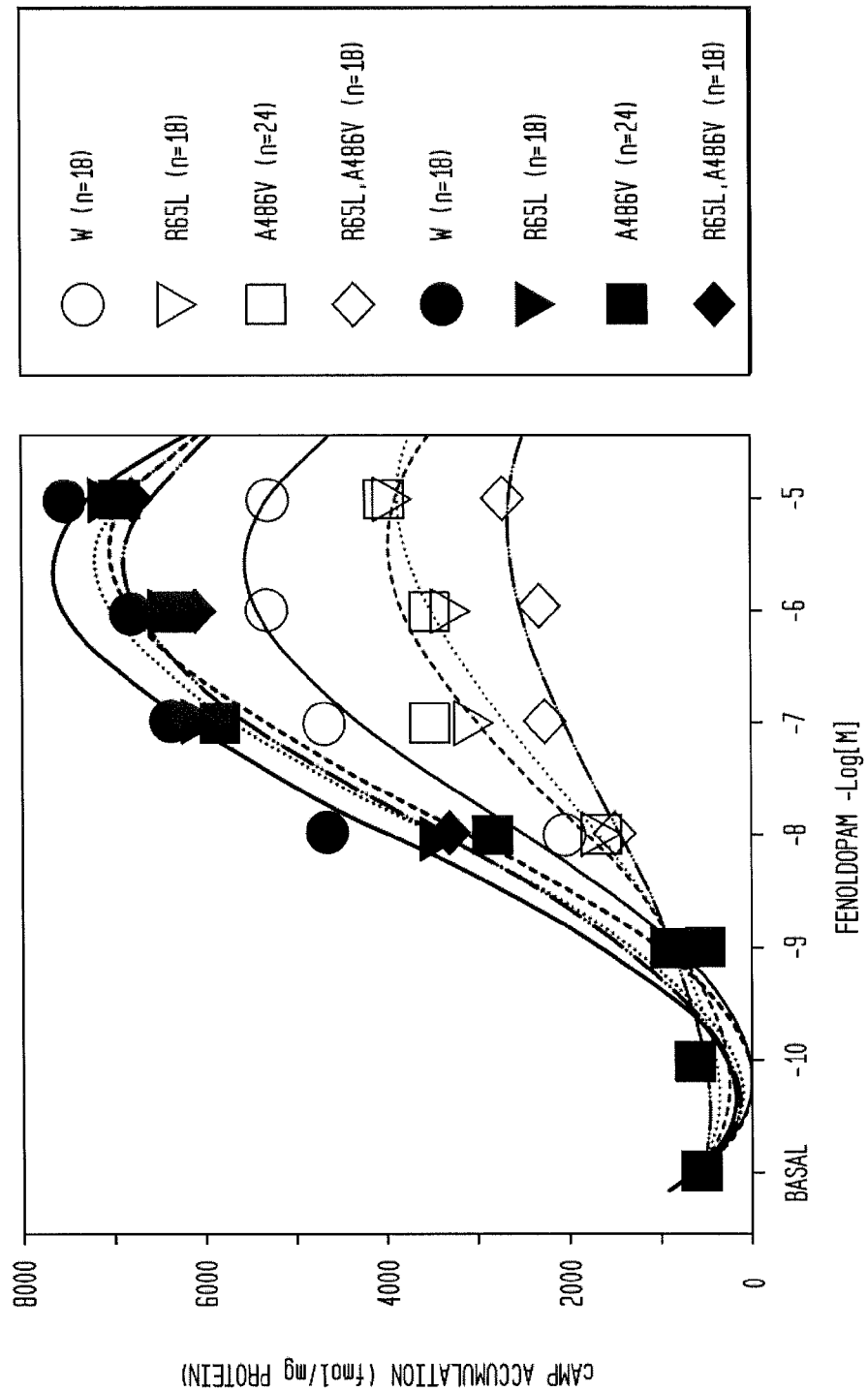
FIG. 5 is a graph that shows that mutations of GRK4γ decrease the ability of the D1 receptor to respond to D1-like agonist stimulation in Chinese hamster ovary cells made to hyperexpress GRK4γ and D1 receptor.

To determine if the variations in the GRK4γ gene have any functional consequences, the effect of $D_1$-like agonist on cAMP production in Chinese hamster ovary (CHO) cells transfected with both the $D_1$ receptor and wild type or variant GRK4γ[α] cDNA was studied. GRK4δ was used for comparison. The dose response curve in CHO cells in the absence of GRK4γ (vide infra) or GRK4α was similar to those noted with HEK-293 cells, a cell with low endogenous GRK activity. Premont et al., supra. The expression of wild type GRK4γ decreased the ability of the $D_1$ receptor agonist to stimulate cAMP production (FIG. 5, wherein the filled symbols represent controls wherein the GRK4γ was turned off). However, the inhibition of the $D_1$ agonist action became even greater with the GRK4γ variants R65L, A142V and/or A486V. The effect of wild type or variant GRK4γ was not due to differences in the quantity of the expression of either the $D_1$ receptor or GRK4γ (data not shown). Wild type GRK4γ or its variants did not affect the ability of forskolin to stimulate cAMP accumulation indicating specificity of the interaction of GRK4γ with the $D_1$ receptor. The action of fenoldopam was selective for the $D_1$ receptor since the fenoldopam effect was blocked by the $D_1$-like receptor antagonist SCH23390 (data not shown). In other studies, there was no effect of wild type GRK4δ on $D_1$-like agonist-mediated cAMP accumulation (data not shown) compared to the desensitization of the $D_1$ receptor induced by the wild type GRK4γ. The functional studies in renal proximal tubule cells and the expression studies in CHO cells suggest that an increased activity of GRK4γ is responsible for the decreased ability of $D_1$ receptor ligands to couple to effector enzymes and ion transport proteins in hypertension. In turn, the desensitization of the $D_1$ receptor in renal proximal tubules in hypertension may lead to a decreased ability of the kidney to eliminate a sodium chloride load. The failure of the kidney to excrete sodium chloride is thought to be crucial in the development of hypertension. Guyton, A. C., *Circulatory Physiology III, Arterial Pressure and Hypertension*, W.B. Saunders Co., Philadelphia, Pa. (1980); Guidi et al., J. Am. Soc. Nephrol. 7:1131-1138 (1996). Indeed, genes that regulate renal sodium transport have been shown to be important in the regulation of blood pressure. Lifton, Science 272:676-680 (1996) and Karet et al., Recent Prog. Horm. Res. 52:263-276 (1997).

To determine if the infusion of a substance or agent into a living being that caused the reduction in GRK4 activity could serve as an antihypertensive therapeutic, further experiments were conducted in the spontaneously hypertensive rat (SHR). Six male rats, 4 weeks of age, weighing 100 g were subjected to a left uninephrectomy and then allowed two weeks to recover from surgery. After recovery, a 30 day osmotic minipump equipped with a single outlet catheter was filled with either phosphorotioate/propyne-modified antisense GRK4 oligonucleotide (5 nM, one microliter/hr) or scrambled GRK4 oligonucleotide and then was implanted into the renal cortex of the remaining left kidney. The outlet of the catheter was inserted approximately 1 mm deep into the renal cortex of the remaining kidney and secured with Superglue. The rats were then allowed to recover from surgery and daily measurements were made for blood pressure and urine output (volume and electrolytes). After 30 days, the rats were sacrificed and their remaining kidney was used for Western blot analysis of GRK4. Our studies demonstrated that blood pressure was reduced in rats treated with antisense oligonucleotide to GRK4 (n=3) when compared to rats treated with scrambled GRK4 oligonucleotide (n=3). Furthermore, it was demonstrated by Western blot analysis that antisense oligonucleotides reduced the expression of renal GRK4.

In conclusion, the examples demonstrate a $D_1$ receptor/adenylyl cyclase coupling defect in renal proximal tubule cells from subjects with essential hypertension. Increased GRK activity in renal proximal tubule cells in human essential hypertension is due to activating missense variations of GRK4, an effect that was reproduced in a transfected cell model. Moreover, preventing the translation of GRK4 normalized the coupling of the $D_1$ receptor to adenylyl cyclase in hypertension. Again, without intending to be bound by any particular theory of operation, Applicants believe that the homozygous amino acid variations cause a ligand independent serine-phosphorylation of the $D_1$ receptor which results in its uncoupling from the G protein/effector complex. The desensitization of the $D_1$ receptor in the renal proximal tubule may be the cause of the compromised natriuretic effect of dopamine that eventually leads to sodium retention and hypertension. These conclusions are supported by the results of experiments described above demonstrating that intrarenal infusion of spontaneous hypertensive rats (SHR) with antisense oligonucleotides to GRK4 results in an intrarenal reduction in the concentration of GRK4 and lowering of their mean arterial blood pressure. Thus, substances or agents that alter the concentration or activity of GRK4 represent a novel class of antihypertensive medications.

A nephron segment-specific defective coupling between the dopamine D1A receptor and the G protein/effector enzyme complex may be a cause of the renal sodium retention in spontaneously hypertensive rats (SHR). The decreased ability of exogenous and renal endogenous dopamine to inhibit sodium transport in renal proximal tubules co-segregates with hypertension in F2 crosses of SHR and its normotensive control, the Wistar-Kyoto (WKY) rat. Similar defects were found in the Dahl salt-sensitive rat and more importantly, in humans with essential hypertension. Thus, primary cultures of renal proximal tubules cells from hypertensive humans have a defective coupling of a renal D1-like receptor to adenylyl cyclase (AC), similar to the coupling defect found in hypertensive rodents. These in vitro data are in agreement with in vivo studies demonstrating a defective D1-like receptor from the G protein/effector enzyme complex is not due to homologous or heterologous desensitization, receptor down-regulation, G protein or effector enzyme "defects" or a mutation in the primary sequence of the D1-like receptors. Rather, the uncoupling of the D1-like receptor is due to a ligand-independent hyper-phosphorylation of the D-1 receptor (the major D1-like receptor in the kidney) due to homozygous mutations of GRK4 isoform with limited organ and nephron expression.

The diagnostic tests of the present invention will screen individuals to identify those predisposed to essential hypertension. Genetic, cellular and biochemical tools in which to carry out these tests are also provided. The present invention also provides for several tools and methods for conducting drug discovery and identification of substances with anti-hypertensive activity or properties. The compositions and methods for normalizing sodium transport in kidney cells of individuals having essential hypertension provide means to treat this disease.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A transgenic mouse, whose genome comprises a transgene encoding a gamma (γ) isoform of GRK4 protein which is expressed in renal cells to produce said GRK4γ isoform of said protein containing at least one polymorphism comprising A142V, and wherein expression of said transgene causes said transgenic mouse to exhibit a state of essential hypertension compared to a normotensive mouse whose renal cells do not express said GRK4γ isoform of said protein.

2. The transgenic mouse of claim 1, wherein said renal cells have a decreased ability to reject sodium compared to a normotensive mouse whose renal cells do not express said GRK4 protein.

3. A method of identifying putative anti-hypertensive agents, comprising:
    comparing electrolyte output of a first transgenic mouse of claim 1 administered said agent with the electrolyte output of a second transgenic mouse of claim 1 not administered said agent, whereby an increase in the electrolyte output of said first transgenic mouse compared to said second transgenic mouse identifies a candidate anti-hypertensive agent.

4. A transgenic mouse whose genome comprises a transgene encoding a gamma (γ) isoform of GRK4 protein which is expressed in renal cells to produce said GRK4γ isoform of said protein containing at least one polymorphism comprising A486V, and wherein expression of said transgene and exposure to a high-salt diet causes said transgenic mouse to exhibit a state of essential hypertension compared to a normotensive mouse whose renal cells do not express said GRK4γ isoform of said protein.

5. A method of identifying putative anti-hypertensive agents, comprising: comparing electrolyte output of a first transgenic mouse of claim 4 administered said agent with the electrolyte output of a second transgenic mouse of claim 4 not administered said agent, whereby an increase in the electrolyte output of said first transgenic mouse compared to said second transgenic mouse identifies a candidate anti-hypertensive agent, wherein the first and second transgenic mice are administered said agent subsequent to exposure to a high-salt diet and exhibition of a state of essential hypertension.

* * * * *